United States Patent
Furuya et al.

(10) Patent No.: US 9,664,618 B2
(45) Date of Patent: May 30, 2017

(54) PARTICLE DETECTOR

(71) Applicant: Azbil Corporation, Chiyoda-ku (JP)

(72) Inventors: Masashi Furuya, Chiyoda-ku (JP); Daisuke Obara, Chiyoda-ku (JP)

(73) Assignee: AZBIL CORPORATION, Chiyoda-ku (JP)

( * ) Notice: Subject to any disclaimer, the term of this patent is extended or adjusted under 35 U.S.C. 154(b) by 0 days.

(21) Appl. No.: 15/047,354

(22) Filed: Feb. 18, 2016

(65) Prior Publication Data

US 2016/0238530 A1  Aug. 18, 2016

(30) Foreign Application Priority Data

Feb. 18, 2015  (JP) .................................. 2015-029999

(51) Int. Cl.
| | | |
|---|---|---|
| *F21V 9/16* | (2006.01) | |
| *G01N 21/64* | (2006.01) | |
| *G01N 15/14* | (2006.01) | |
| *G01N 15/00* | (2006.01) | |
| *G01N 15/10* | (2006.01) | |

(Continued)

(52) U.S. Cl.
CPC ....... *G01N 21/645* (2013.01); *G01N 15/1434* (2013.01); *G01N 15/1459* (2013.01); *G01N 21/53* (2013.01); *G01N 2015/0053* (2013.01); *G01N 2015/1006* (2013.01); *G01N 2021/052* (2013.01)

(58) Field of Classification Search
CPC ............. G01N 15/147; G01N 15/1459; G01N 2015/1493; G01N 21/3563; G01N 15/14; G01N 15/1436; G01N 15/1463; G01N 15/0211; G01N 21/53; G01N 15/1475; G01N 2201/068; G01N 15/1404; G01N 2201/061
USPC ...................................................... 250/458.1
See application file for complete search history.

(56) References Cited

U.S. PATENT DOCUMENTS

| | | | | |
|---|---|---|---|---|
| 5,412,466 A | * | 5/1995 | Ogino ................ | G01N 15/1404 356/246 |
| 5,825,477 A | * | 10/1998 | Furuie ................ | G01N 15/0227 356/335 |

(Continued)

FOREIGN PATENT DOCUMENTS

| | | |
|---|---|---|
| JP | 4540509 | 7/2010 |
| JP | 2013-122397 | 6/2013 |
| WO | 2010/080642 | 7/2010 |

*Primary Examiner* — David J Makiya
*Assistant Examiner* — Taeho Jo
(74) *Attorney, Agent, or Firm* — Oblon, McClelland, Maier & Neustadt, L.L.P.

(57) ABSTRACT

A particle detector that includes a flow cell that includes a through hole having a circular sectional shape and allowing a fluid containing a particle to flow therethrough, an inspection light source that irradiates the flow cell with inspection light in a direction perpendicular to an extending direction of the through hole, and an optical detector that detects reaction light generated by the particle and which exits the flow cell so as to be angled relative to a sector-shaped plane which has a vertex at an intersection point of the inspection light and the through hole of the flow cell, is parallel to an optical path of the inspection light, and is perpendicular to the extending direction of the through hole of the flow cell.

6 Claims, 33 Drawing Sheets

(51) Int. Cl.
*G01N 21/05* (2006.01)
*G01N 21/53* (2006.01)

(56) References Cited

U.S. PATENT DOCUMENTS

| | | | | |
|---|---|---|---|---|
| 6,104,483 | A * | 8/2000 | Sebok | G01N 21/05 356/244 |
| 6,184,517 | B1 * | 2/2001 | Sawada | G01N 15/0205 250/222.2 |
| 6,482,652 | B2 * | 11/2002 | Furlong | B07C 5/3425 209/3.1 |
| 7,355,706 | B2 | 4/2008 | Girvin et al. | |
| 8,189,187 | B2 | 5/2012 | Graham et al. | |
| 9,267,887 | B2 * | 2/2016 | Kanomata | G01N 21/64 |
| 2004/0011975 | A1 * | 1/2004 | Nicoli | G01N 15/0227 250/574 |
| 2005/0068536 | A1 * | 3/2005 | Schwabe | B01L 3/502715 356/436 |
| 2006/0001875 | A1 * | 1/2006 | Christodoulou | G01N 15/1459 356/342 |
| 2006/0132770 | A1 * | 6/2006 | Girvin | G01N 15/1459 356/338 |
| 2009/0029870 | A1 * | 1/2009 | Ward | G01N 15/1404 506/9 |
| 2011/0066382 | A1 * | 3/2011 | Adams | G01N 15/147 702/19 |
| 2011/0127444 | A1 * | 6/2011 | Ozasa | G01N 15/147 250/458.1 |
| 2011/0235030 | A1 * | 9/2011 | Champseix | G01N 15/1209 356/243.2 |
| 2011/0291025 | A1 * | 12/2011 | Fortin | G01N 15/1436 250/458.1 |
| 2012/0140221 | A1 | 6/2012 | Salton | |
| 2012/0196356 | A1 * | 8/2012 | Wagner | C12N 5/0612 435/288.7 |
| 2013/0077087 | A1 | 3/2013 | Janka et al. | |
| 2013/0161243 | A1 * | 6/2013 | Kanomata | G01N 30/74 210/85 |
| 2014/0030696 | A1 * | 1/2014 | Luscher | G01N 15/1404 435/3 |
| 2014/0234865 | A1 * | 8/2014 | Gabriel | G01N 33/5008 435/7.21 |
| 2015/0233812 | A1 * | 8/2015 | Yan | G01N 15/1434 250/214.1 |
| 2016/0252443 | A1 * | 9/2016 | Spriggs | G01N 15/1456 356/336 |

* cited by examiner

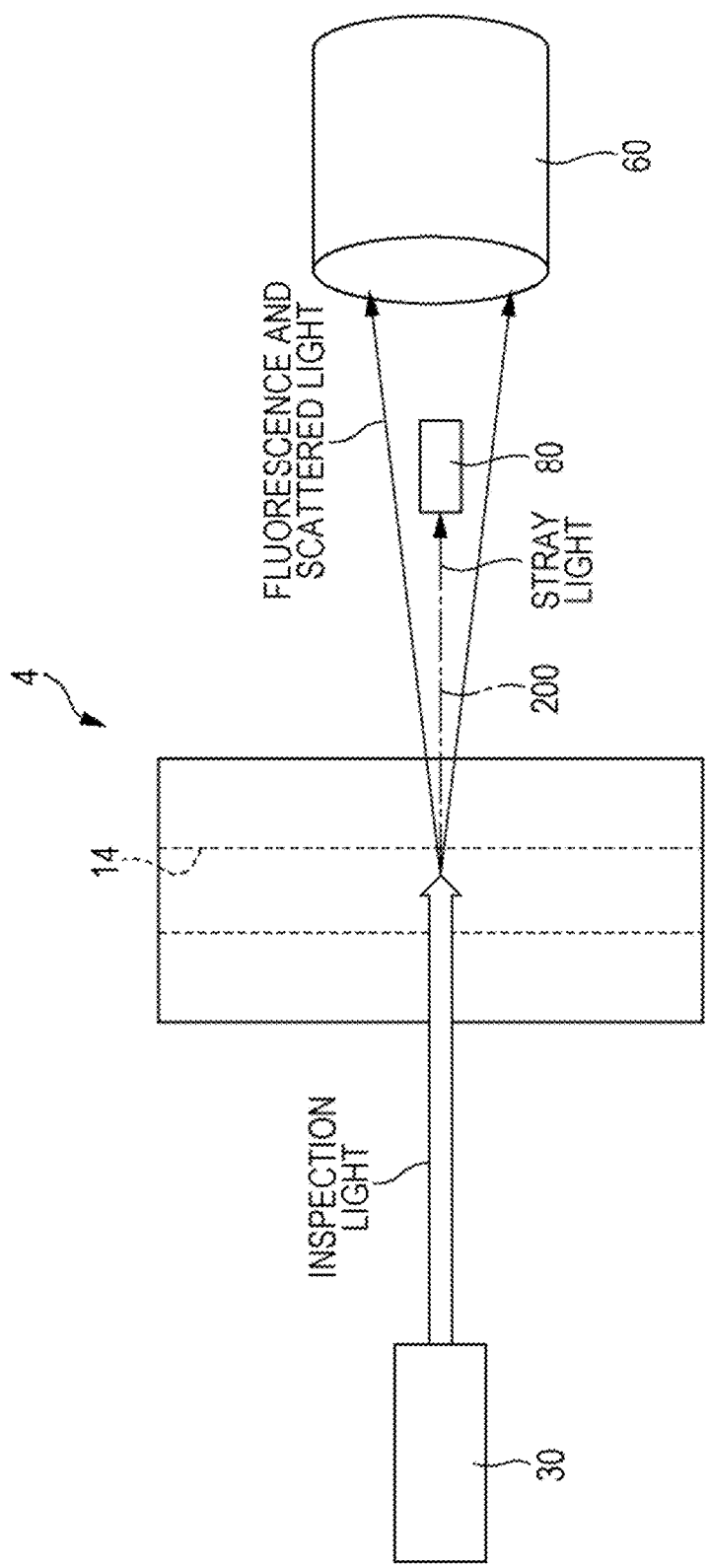

PARTICLE DETECTOR

CROSS-REFERENCE TO RELATED APPLICATIONS

This application claims priority to Japanese Application No. 2015-029999, filed Feb. 18, 2015, the entire contents of which are incorporated herein by reference.

BACKGROUND

1. Field of the Disclosure

The present disclosure relates to a detection technique and a particle detector.

2. Description of the Related Art

Flow cells that allow a fluid as a sample to flow therethrough are used for particle detectors including, for example, flow cytometers and microorganism detectors. Such a flow cell is transparent, and when a fluid flowing through the flow cell is irradiated with light, particles contained in the fluid emit fluorescence and scattered light. The fluorescence and the scattered light are condensed by a lens disposed next to the flow cell so as to be detected (see, for example, Japanese Patent No. 4540509, US Patent Application Publication No. 2012/0140221, U.S. Pat. No. 7,355,706, International Publication No. 2010/080642, U.S. Pat. No. 8,189,187, and Japanese Unexamined Patent Application Publication No. 2013-122397). The number and the type of the particles contained in the fluid can be identified by the number of times of detection, detected intensity, a detected wavelength, and so forth of the fluorescence and the scattered light. For example, whether or not the particles are a biological particle, whether or not the particles are resin, whether or not the particles are an air bubble, and so forth can be determined. There also is a case in which an airflow is irradiated with light so as to detect particles contained in the airflow without using the flow cell (for example, see US Patent Application Publication No. 2013/0077087).

SUMMARY

According to one aspect of the disclosure, there is provided a particle detector that includes a flow cell that is transparent and includes a through hole having a circular sectional shape, the through hole being configured to allow a fluid containing a particle to flow therethrough, an inspection light source configured to irradiate the flow cell with inspection light in a direction perpendicular to an extending direction of the through hole, and an optical detector configured to detect reaction light generated by the particle irradiated with the inspection light in the flow cell, the reaction light exiting the flow cell so as to be angled relative to a sector-shaped plane, wherein the sector-shaped plane has a vertex at an intersection point of the inspection light and the through hole of the flow cell, is parallel to an optical path of the inspection light, and is perpendicular to the extending direction of the through hole of the flow cell.

BRIEF DESCRIPTION OF THE DRAWINGS

FIG. 35 is a schematic view of a particle detector according to a ninth embodiment of the present disclosure.

DESCRIPTION OF THE EMBODIMENTS

Figure 1:
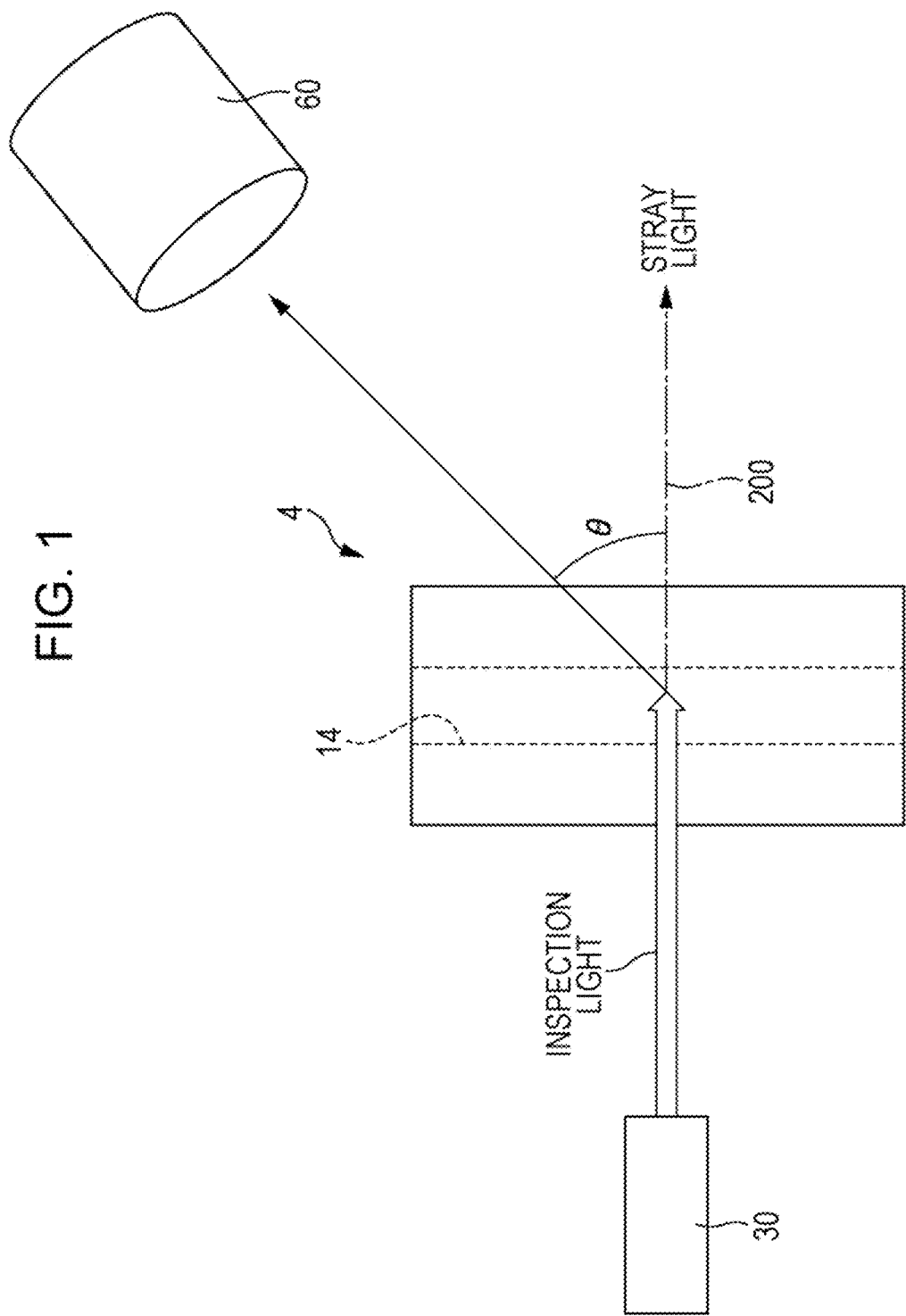
FIG. 1 is a schematic view of a particle detector according to a first embodiment of the present disclosure.

When the flow cell is irradiated with light, stray light may be generated due to reflection and refraction of the light at the flow cell. The stray light may obstruct detection of the fluorescence and the scattered light generated by the particles. Accordingly, one of objects of the present disclosure is that a particle detector with which the effects of stray light can be suppressed can be provided.

According to a first aspect of the present disclosure, a particle detector includes (a) an inspection light source that emits inspection light, (b) a flow cell that is transparent, that has a through hole which has a circular sectional shape and which allows a fluid containing a particle to flow through the through hole, and that is irradiated with the inspection light in a direction perpendicular to an extending direction of the through hole, and (c) an optical detector that detects reaction light which is generated by the particle irradiated with the inspection light in the flow cell and which exits the flow cell so as to be angled relative to a sector-shaped plane which has a vertex at an intersection point of the inspection light and the through hole of the flow cell, which is parallel to an optical path of the inspection light, and which is perpendicular to the extending direction of the through hole of the flow cell.

In the above-described particle detector, the optical detector may be disposed at an angle relative to the sector-shaped plane which has the vertex at the intersection point of the inspection light and the through hole of the flow cell, is parallel to the optical path of the inspection light, and is perpendicular to the extending direction of the through hole of the flow cell. The above-described particle detector may further include a condensing optical system that condenses the reaction light which exits the flow cell so as to be angled relative to the sector-shaped plane which has the vertex at the intersection point of the inspection light and the through hole of the flow cell, is parallel to the optical path of the inspection light, and is perpendicular to the extending direction of the through hole of the flow cell. The condensing optical system may include a lens disposed at an angle relative to the sector-shaped plane which has the vertex at the intersection point of the inspection light and the through hole of the flow cell, is parallel to the optical path of the inspection light, and is perpendicular to the extending direction of the through hole of the flow cell.

In the above-described particle detector, the flow cell may include a semispherical lens portion through which the reaction light passes the flow cell may include a semispherical reflective film that reflects the reaction light generated by the particle irradiated with the inspection light. The semispherical reflective film may have a cut at a portion thereof where the semispherical reflective film intersects the sector-shaped plane which has the vertex at the intersection point of the inspection light and the through hole of the flow cell, is parallel to the optical path of the inspection light, and is perpendicular to the extending direction of the through hole of the flow cell. Alternatively, the semispherical reflective film does not necessarily intersect the sector-shaped plane which has the vertex at the intersection point of the inspection light and the through hole of the flow cell, is parallel to the optical path of the inspection light, and is perpendicular to the extending direction of the through hole of the flow cell.

In the above-described particle detector, the flow cell may include a plate-shaped member that is transparent, that is perpendicular to the through hole of the flow cell, that has the through hole, and that is disposed so as to include part of a plane which includes the optical path of the inspection light. The plate-shaped member of the flow cell may include a first main surface and a second main surface that faces the first main surface, the through hole of the plate-shaped member may be a first part of the through hole which penetrates through the plate-shaped member from the first main surface to the second main surface, and the flow cell may further include a first semispherical member and a second semispherical member. In this case, the first semispherical member is transparent, has a second part of the through hole, and is disposed on the first main surface of the plate-shaped member such that the first part of the through hole and the second part of the through hole communicate with each other, and the second semispherical member is transparent, has a third part of the through hole, and is disposed on the second main surface of the plate-shaped member such that the first part of the through hole and the third part of the through hole communicate with each other. A width of each of the first main surface and the second main surface of the plate-shaped member may be larger than a width of a bottom surface of the first semispherical member and a width of a bottom surface of the second semispherical member. The flow cell may further include a semispherical reflective film that covers the first semispherical member.

The above-described particle detector may further include an elliptical mirror that reflects the reaction light which exits the flow cell. The elliptical mirror may have a cut at a portion thereof where the elliptical mirror intersects the sector-shaped plane which has the vertex at the intersection point of the inspection light and the through hole of the flow cell, is parallel to the optical path of the inspection light, and is perpendicular to the extending direction of the through hole of the flow cell. Alternatively, the elliptical mirror does not necessarily intersect the sector-shaped plane which has the vertex at the intersection point of the inspection light and the through hole of the flow cell, is parallel to the optical path of the inspection light, and is perpendicular to the extending direction of the through hole of the flow cell.

According to a second aspect of the present disclosure, a particle detector includes (a) an inspection light source that emits inspection light, (b) a flow cell that is transparent, that has a through hole which has a circular sectional shape and which allows a fluid containing a particle to flow therethrough, that is irradiated with the inspection light in a direction perpendicular to an extending direction of the through hole, and that includes a projection including an optical path of the inspection light, and (c) an optical detector that detects reaction light generated by the particle irradiated with the inspection light in the flow cell.

In the above-described particle detector, the optical detector may be disposed at an angle relative to the projection of the flow cell. The above-described particle detector may further include a condensing optical system that condenses the reaction light which exits the flow cell so as to be angled relative to the projection of the flow cell. The condensing optical system may include a lens disposed at an angle relative to the projection of the flow cell.

In the above-described particle detector, the flow cell may include a plate-shaped member that is transparent, that is perpendicular to the through hole of the flow cell, that has the through hole, and that is disposed so as to include part of a plane which includes the optical path of the inspection light. The plate-shaped member of the flow cell may include a first main surface and a second main surface that faces the first main surface, the through hole of the plate-shaped member may be a first part of the through hole which penetrates through the plate-shaped member from the first main surface to the second main surface, and the flow cell may further include a first semispherical member and a second semispherical member. In this case, The first semispherical member is transparent, has a second part of the through hole, and is disposed on the first main surface of the plate-shaped member such that the first part of the through hole and the second part of the through hole communicate with each other, and the second semispherical member is transparent, has a third part of the through hole, and is disposed on the second main surface of the plate-shaped member such that the first part of the through hole and the third part of the through hole communicate with each other. A width of each of the first main surface and the second main surface of the plate-shaped member may be larger than a width of a bottom surface of the first semispherical member and a width of a bottom surface of the second semispherical member, and a portion of the plate-shaped member beyond the width of the first semispherical member and the width of the second semispherical member may serve as the projection of the flow cell. The flow cell may further include a semispherical reflective film that covers the first semispherical member.

The above-described particle detector may further include an elliptical mirror that reflects the reaction light which exits the flow cell. The elliptical mirror does not necessarily intersect the projection of the flow cell.

Furthermore, according to a third aspect of the present disclosure, a particle detector includes (a) an inspection light source that emits inspection light, (b) a flow cell that is transparent, that has a through hole which has a circular sectional shape and which allows a fluid containing a particle to flow through the through hole, and that is irradiated with the inspection light in a direction perpendicular to an extending direction of the through hole, (c) a stray light attenuation member that is disposed so as to include a sector-shaped plane which has a vertex at an intersection point of the inspection light and the through hole of the flow cell, which is parallel to an optical path of the inspection light, and which is perpendicular to the extending direction of the through hole of the flow cell, and (d) an optical detector that is disposed farther from the flow cell than the stray light attenuation member in a rearward direction and that detects the reaction light generated by the particle irradiated with the inspection light in the flow cell.

In the above-described particle detector, a width of the stray light attenuation member may be smaller than a width of a light receiving surface of the optical detector in a direction parallel to the extending direction of the through hole of the flow cell.

According to the present disclosure, the particle detector with which the effects of the stray light can be suppressed can be provided.

Embodiments of the present disclosure will be described below. In the drawings referred to below, the same or similar elements are denoted by the same or similar signs. Also, the drawings are schematic. Accordingly, it should be understood that specific dimensions and the like are determined in view of the following description. In addition, of course, the relationships or the ratios of the dimensions may differ between the drawings.

First Embodiment

A particle detector according to a first embodiment of the present disclosure includes, as illustrated in FIG. 1, an inspection light source 30, a flow cell 4, and an optical detector 60. The inspection light source 30 emits inspection light. The flow cell 4 is transparent and provided with a through hole 14 that has a circular sectional shape and that allows a fluid containing particles to flow therethrough. The flow cell 4 is irradiated with the inspection light in a direction perpendicular to an extending direction of the through hole 14. The optical detector 60 detects reaction light generated by the particles irradiated with the inspection light in the flow cell 4. This reaction light exits the flow cell 4 so as to be angled at an angle $\theta$ relative to a sector-shaped plane 200 which has a vertex at an intersection point of the inspection light and the through hole 14 of the flow cell 4, is parallel to an optical path of the inspection light, and is perpendicular to the extending direction of the through hole 14 of the flow cell 4.

The flow cell 4 has, for example, a rectangular parallelepiped shape. The through hole 14 perpendicularly extends between surfaces of the flow cell 4 facing each other. Surfaces of the flow cell 4 and an inner wall of the through hole 14 are, for example, ground. The through hole 14 passes through, for example, the center of the flow cell 4. By forming the through hole 14 to have a circular sectional shape so that no angle is formed in the inner wall, accumulation of bubbles and adhesion of contamination inside the through hole 14 can be suppressed. The extending direction of the through hole 14 is perpendicular to a traveling direction of the inspection light. The diameter of the through hole 14 is, although it is not limited to this, for example, less than 1 mm. The flow cell 4 is formed of, for example, silica glass.

The particles contained in the fluid flowing through the flow cell 4 include, for example, biological substances including microorganisms and the like, cells, chemical substances, dust such as pieces of refuse, motes, and dirt. Examples of the microorganisms include bacteria and fungi. Examples of the bacteria include Gram-negative bacteria and Gram-positive bacteria. Examples of the Gram-negative bacteria include colon *bacilli*. Examples of the Gram-positive bacteria include *Staphylococcus epidermidis, Bacillus subtilis, micrococci,* and *corynebacteria*. Examples of fungi include *Aspergillus* such as black patches. Despite the above description, the microorganisms are not limited to the above-described microorganisms.

In the case where fluorescent particles such as microorganisms are contained in the fluid, the particles emit fluorescence when the particles are irradiated with excitation light. For example, riboflavin, flavin mononucleotide (FMN), flavin adenine dinucleotide (FAD), nicotinamide adenine dinucleotide phosphate (NAD (P) H), pyridoxamine, pyridoxal-5'-phosphate, pyridoxine, tryptophan, tyrosine, phenylalanine, and so forth contained in the microorganisms emit fluorescence.

The excitation light as the inspection light for detecting the fluorescent particles flowing through the flow cell 4 is radiated from the inspection light source 30 so as to be focused on, for example, the center of the flow cell 4. The inspection light may be collimated light. A light emitting diode (LED) or a laser may be used as the inspection light source 30. The wavelength of the inspection light is, for example, from 250 to 550 nm. The inspection light may be visible light or ultraviolet light. When the inspection light is visible light, the wavelength of the inspection light is, for example, in a range from 400 to 550 nm. An example of such a wavelength is 405 nm. When the inspection light is ultraviolet light, the wavelength of the inspection light is, for example, in a range from 300 to 380 nm. An example of such a wavelength is 340 nm. However, the wavelength of the inspection light is not limited to any of the above-described wavelengths.

The fluorescent particles irradiated with the inspection light in the through hole 14 that serves as an inspection region emit fluorescence. Furthermore, scattered light is generated due to, for example, Mie scattering with the fluorescent particles and non-fluorescent particles irradiated with the inspection light. The fluorescence and the scattered light as the reaction light generated by the particles irradiated with light are omnidirectionally emitted from the particles.

The optical detector 60 receives and detects the reaction light generated in the flow cell 4. For example, the optical detector 60 is disposed at the angle θ relative to the sector-shaped plane 200. The sector-shaped plane 200 has the vertex at the intersection point of the inspection light and the through hole 14 of the flow cell 4, is parallel to the optical path of the inspection light, and is perpendicular to the extending direction of the through hole 14 of the flow cell 4. For example, a photodiode, a photomultiplier tube, or the like may be used as the optical detector 60. The optical detector 60, upon reception of light, converts light energy into electrical energy.

When the flow cell 4 is irradiated with the inspection light, stray light may be generated due to reflection and refraction of the inspection light at a curved interface between the inner wall of the through hole 14 having a circular section and the fluid in the through hole 14. The stray light tends to diverge in a sector shape having a vertex angle of about 30 to 60 degrees from a vertex at the intersection point of the inspection light and the through hole 14 of the flow cell 4 in a plane perpendicular to the extending direction of the through hole 14 of the flow cell 4. The angle by which the stray light diverges tends to increase as the diameter of the through hole 14 reduces and the width of the inspection light increases.

Unlike Mie scattering caused with the particles flowing through the through hole 14 of the flow cell 4, the stray light is not needed for detection of the particles. Accordingly, when the stray light reaches the optical detector 60, the stray light may cause noise. In order to address this, in the particle detector according to the first embodiment, the optical detector 60 is disposed so as to detect the reaction light which exits the flow cell 4 so as to be angled at the angle θ relative to the sector-shaped plane 200 which has the vertex at the intersection point of the inspection light and the through hole 14 of the flow cell 4, is parallel to the optical path of the inspection light, and is perpendicular to the extending direction of the through hole 14 of the flow cell 4. Thus, the stray light does not reach the optical detector 60. Accordingly, even when the stray light is generated, the generation of noise caused by the stray light can be suppressed.

Figure 2:
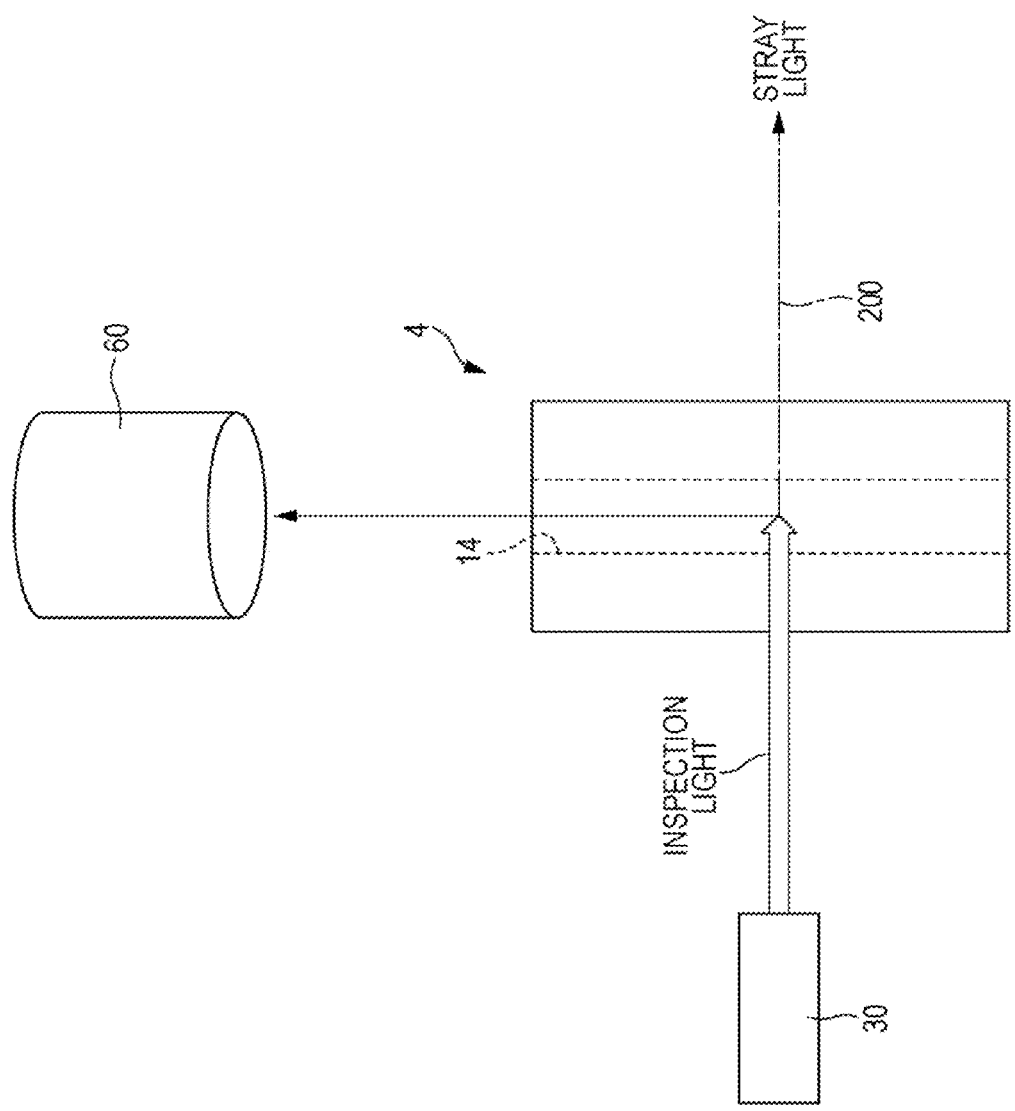
FIG. 2 is a schematic view of the particle detector according to the first embodiment of the present disclosure.

The angle θ at which the optical detector 60 is disposed relative to the sector-shaped plane 200 may foe a right angle as illustrated in FIG. 2.

Figure 3:
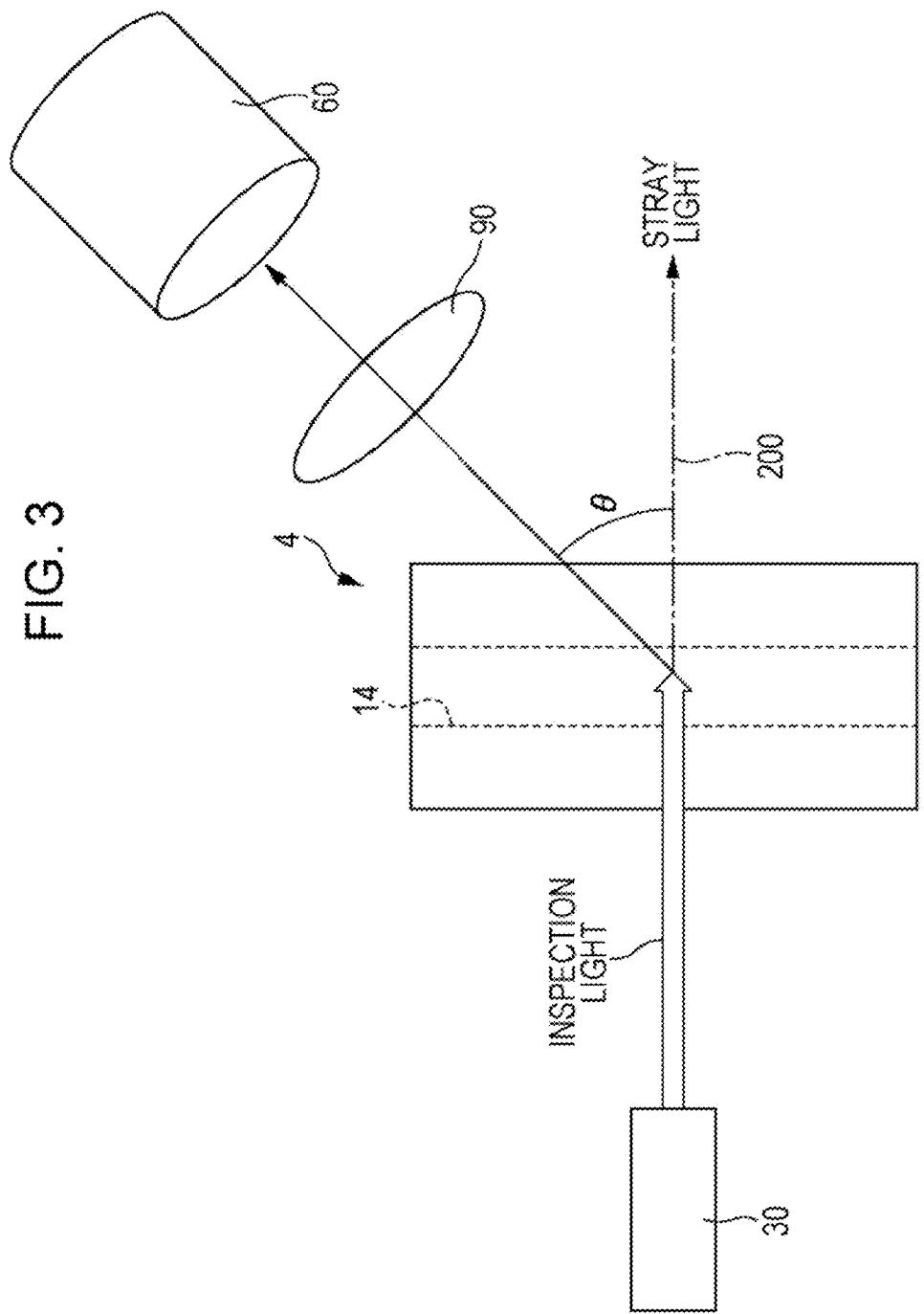
FIG. 3 is a schematic view of the particle detector according to the first embodiment of the present disclosure.

The particle detector according to the first embodiment may further include a condensing optical system. This condensing optical system condenses the reaction light which exits the flow cell 4 so as to be angled at the angle θ relative to the sector-shaped plane 200 which has the vertex at the intersection point of the inspection light and the through hole 14 of the flow cell 4, is parallel to the optical path of the inspection light, and is perpendicular to the extending direction of the through hole 14 of the flow cell 4. As illustrated in FIG. 3, the condensing optical system may include a lens 90 disposed at the angle θ relative to the sector-shaped plane 200. The sector-shaped plane 200 has the vertex at the intersection point of the inspection light and the through hole 14 of the flow cell 4, is parallel to the optical path of the inspection light, and is perpendicular to the extending direction of the through hole 14 of the flow cell 4.

Second Embodiment

Figure 4:
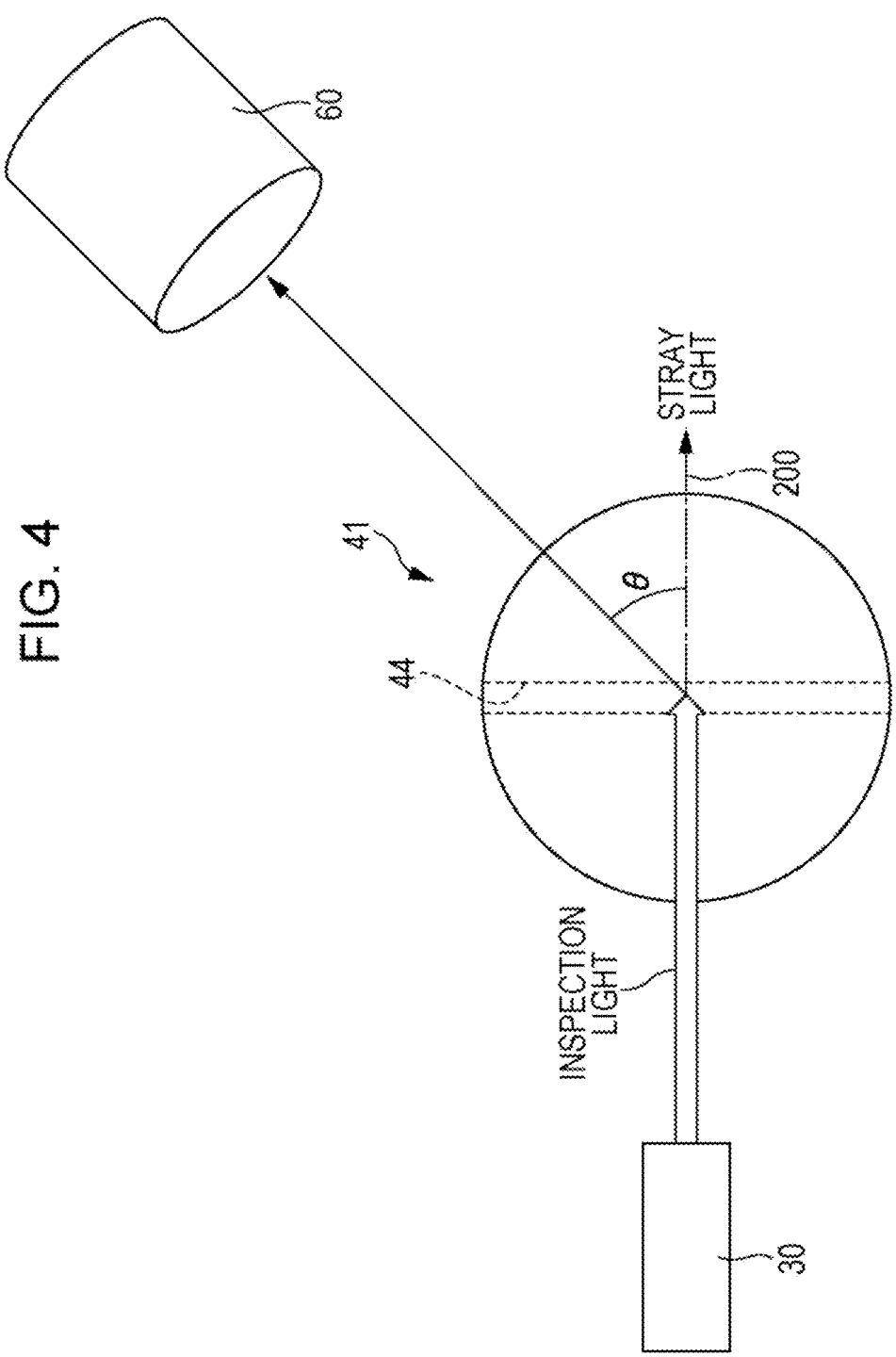
FIG. 4 is a schematic view of a particle detector according to a second embodiment of the present disclosure.

A particle detector according to a second embodiment includes, as illustrated in FIG. 4, a spherical flow cell 41. The flow cell 41 is irradiated with the inspection light in a direction perpendicular to an extending direction of a through hole 44. The optical detector 60 detects the reaction light generated by the particles irradiated with the inspection light in the flow cell 41. This reaction light exits the flow cell 41 so as to be angled at an angle θ relative to the sector-shaped plane 200 which has the vertex at an intersection point of the inspection light and the through hole 44 of the flow cell 41, is parallel to the optical path of the inspection light, and is perpendicular to the extending direction of the through hole 44 of the flow cell 41.

The surface of the spherical flow cell 41 and an inner wall of the through hole 44 are, for example, ground. The through hole 44 passes through, for example, the center of the flow cell 41. The through hole 44 has a circular sectional shape when seen in the extending direction thereof.

The fluorescence and the scattered light generated by the particles irradiated with the inspection light in the through hole 44 of the flow cell 41 are omnidirectionally emitted from the particles. The fluorescence and the scattered light traveling in the flow cell 41 exit through the surface of the flow cell 41. Here, in the case where the flow cell 41 is spherical or substantially spherical and the focus of the inspection light is coincident with or substantially coincident with the center of the flow cell 41, the fluorescence and the scattered light generated at the focus of the inspection light perpendicularly or substantially perpendicularly exit through the surface of the flow cell 41. Thus, with the spherical flow cell 41, losses of the fluorescence and the scattered light caused by reflection and refraction at an interface between the flow cell 41 and external air can be suppressed.

Other elements of the particle detector according to the second embodiment are the same as or similar to those of the first embodiment.

Third Embodiment

Figure 5:
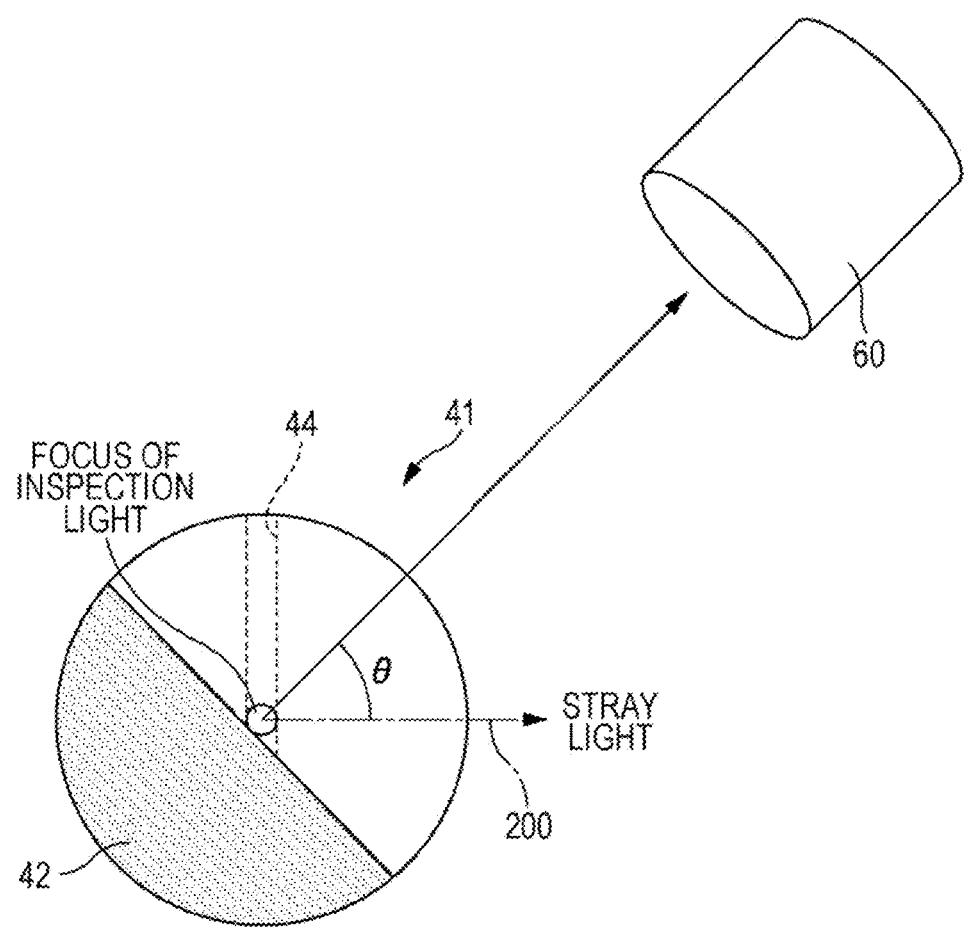
FIG. 5 is a schematic view of a particle detector according to a third embodiment of the present disclosure.

As illustrated in FIG. 5, a particle detector according to a third embodiment includes a semispherical reflective film 42 provided so as to cover part of the spherical flow cell 41. The inspection light is emitted by the inspection light source from the front in a direction perpendicular to the page of FIG. 5 and radiated to the flow cell 41. The inspection light is radiated, for example, so as to be focused on at or near the center of the spherical flow cell 41. The semispherical reflective film 42 covers the flow cell 41 so as not to block an optical path of the inspection light. The semispherical reflective film 42 reflects the reaction light generated by the particles irradiated with the inspection light in the flow cell 41. Part of the flow cell 41 not covered by the semispherical reflective film 42 functions as a semispherical lens portion. The semispherical reflective film 42 and the semispherical lens portion oppose each other.

The semispherical reflective film 42 is, for example, a vapor deposited film and formed of metal or the like. A concave portion of the semispherical reflective film 42 faces the optical detector 60 that detects the reaction light having exited the flow cell 41 or the condensing optical system that condenses the reaction light having exited the flow cell 41.

The reaction light having traveled toward the semispherical lens portion of the flow cell 41 exits through the surface of the semispherical lens portion. Here, in the case where the focus of the inspection light is coincident with the center of the flow cell 41, the fluorescence and the scattered light generated at the focus of the inspection light perpendicularly or substantially perpendicularly exit through the surface of the flow cell 41.

The reaction light having traveled toward the semispherical reflective film 42 of the flow cell 41 is reflected by the semispherical reflective film 42 and exits through the semispherical lens portion. In the case where the focus of the inspection light is coincident with the center of the spherical flow cell 41, the reaction light generated at the focus of the inspection light is perpendicularly or substantially perpendicularly incident upon the semispherical reflective film 42. Thus, the reaction light is perpendicularly or substantially perpendicularly reflected by the semispherical reflective film 42, passes through the center or the substantial center of the spherical flow cell 41, and perpendicularly or substantially perpendicularly exits through the surface of the semispherical lens portion.

Figure 6:
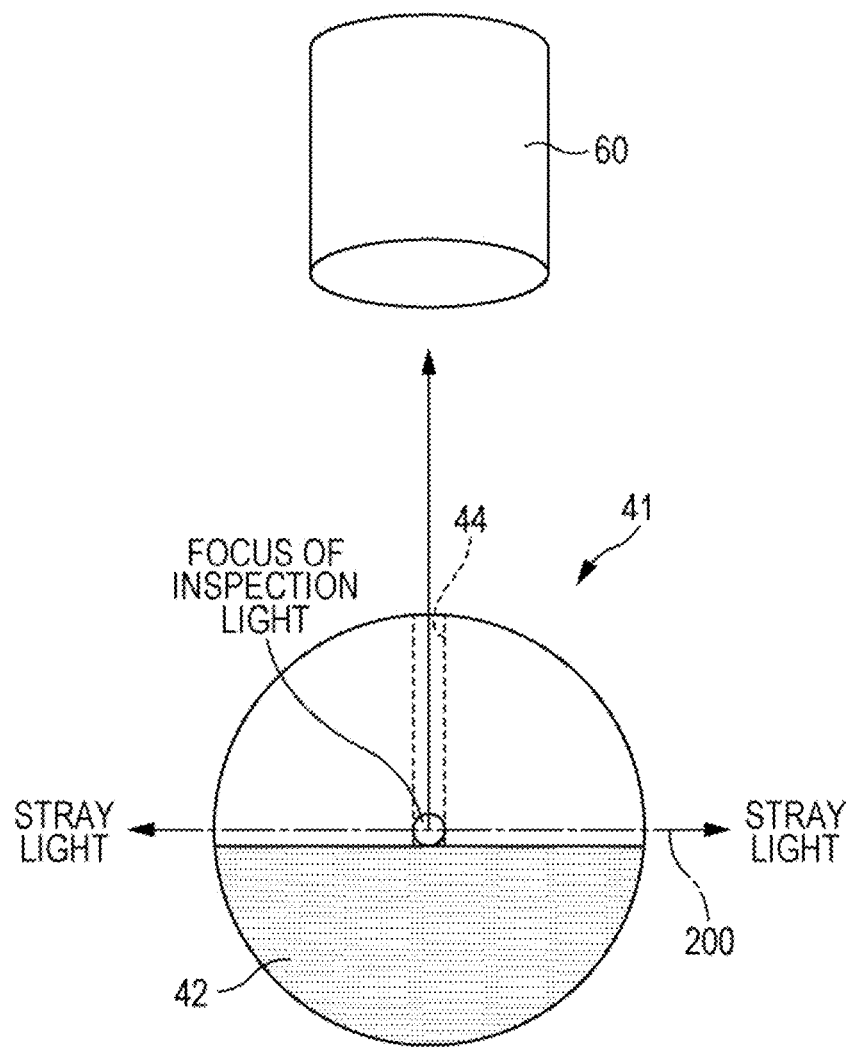
FIG. 6 is a schematic view of the particle detector according to the third embodiment of the present disclosure.

Other elements of the particle detector according to the third embodiment are the same as or similar to those of the second embodiment. Also in the particle detector according to the third embodiment, the angle θ at which the optical detector 60 is disposed relative to the sector-shaped plane 200 may be a right angle as illustrated in FIG. 6. The sector-shaped plane 200 has the vertex at the intersection point of the inspection light and the through hole 44 of the flow cell 41, is parallel to the optical path of the inspection light, and is perpendicular to the extending direction of the through hole 44 of the flow cell 41.

When the flow cell 41 is provided such that, as illustrated in FIG. 6, the semispherical reflective film 42 does not intersect the sector-shaped plane 200 that has the vertex at the intersection point of the inspection light and the through hole 44 of the flow cell 41, is parallel to the optical path of the inspection light, and is perpendicular to the extending direction of the through hole 44 of the flow cell 41, the stray light is not reflected by the semispherical reflective film 42.

Figure 7:
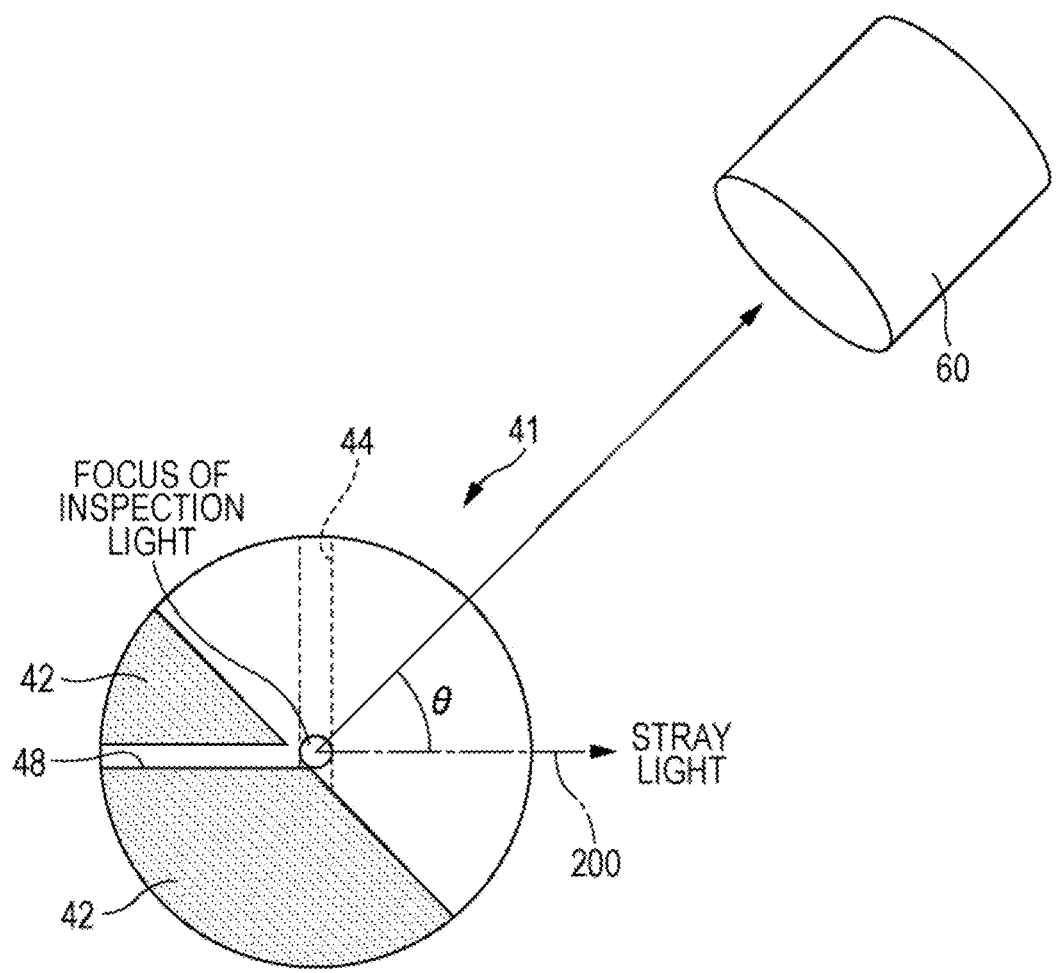
FIG. 7 is a schematic view of the particle detector according to the third embodiment of the present disclosure.

Alternatively, as illustrated in FIG. 7, when the semispherical reflective film 42 has a cut 48 at a portion where the semispherical reflective film 42 intersects the sector-shaped plane 200 that has the vertex at the intersection point of the inspection light and the through hole 44 of the flow cell 41, is parallel to the optical path of the inspection light, and is perpendicular to the extending direction of the through hole 44 of the flow cell 41, the stray light is not reflected by the semispherical reflective film 42.

Fourth Embodiment

Figure 8:
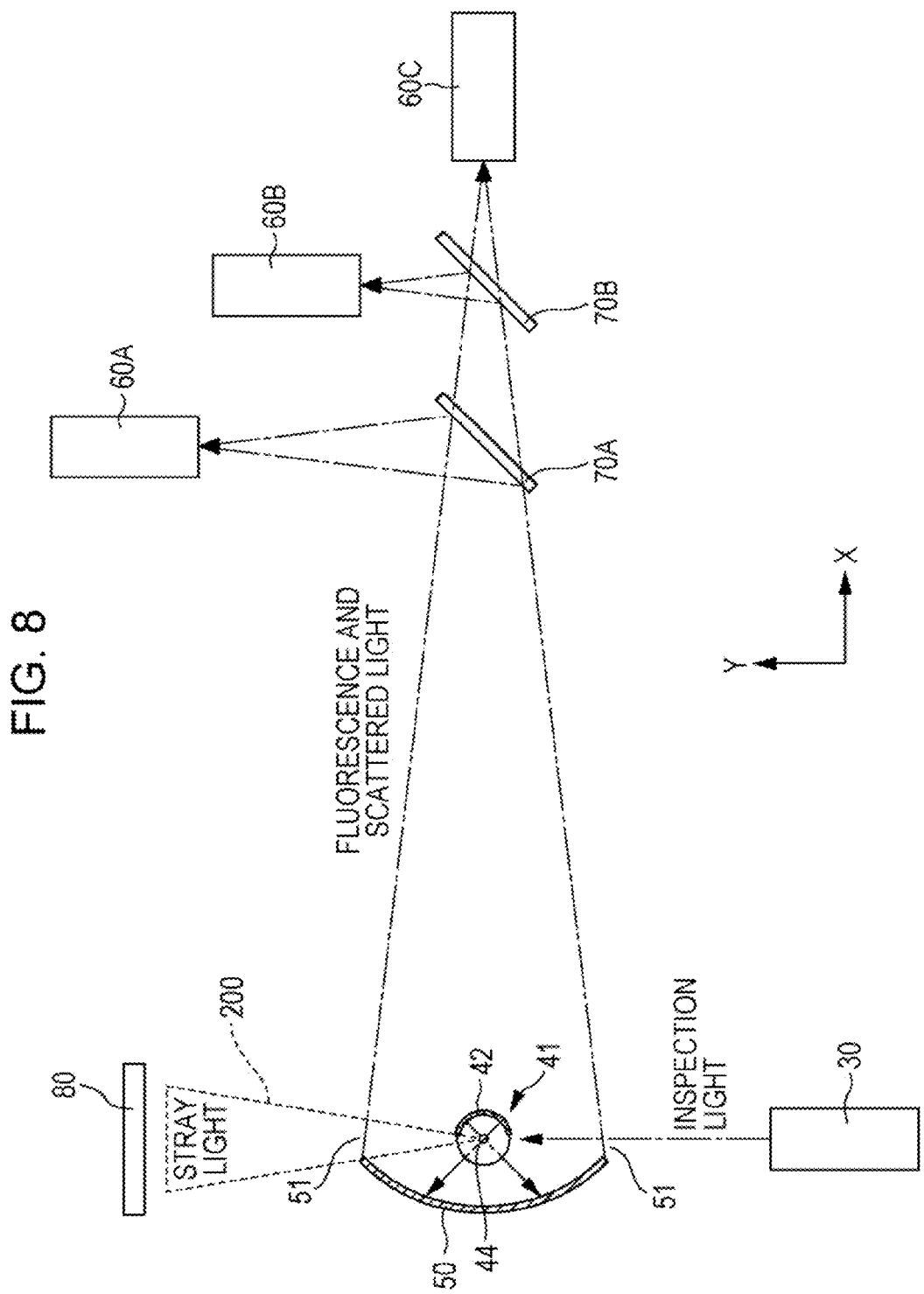
FIG. 8 is a schematic view of a particle detector according to a fourth embodiment of the present disclosure.
Figure 9:
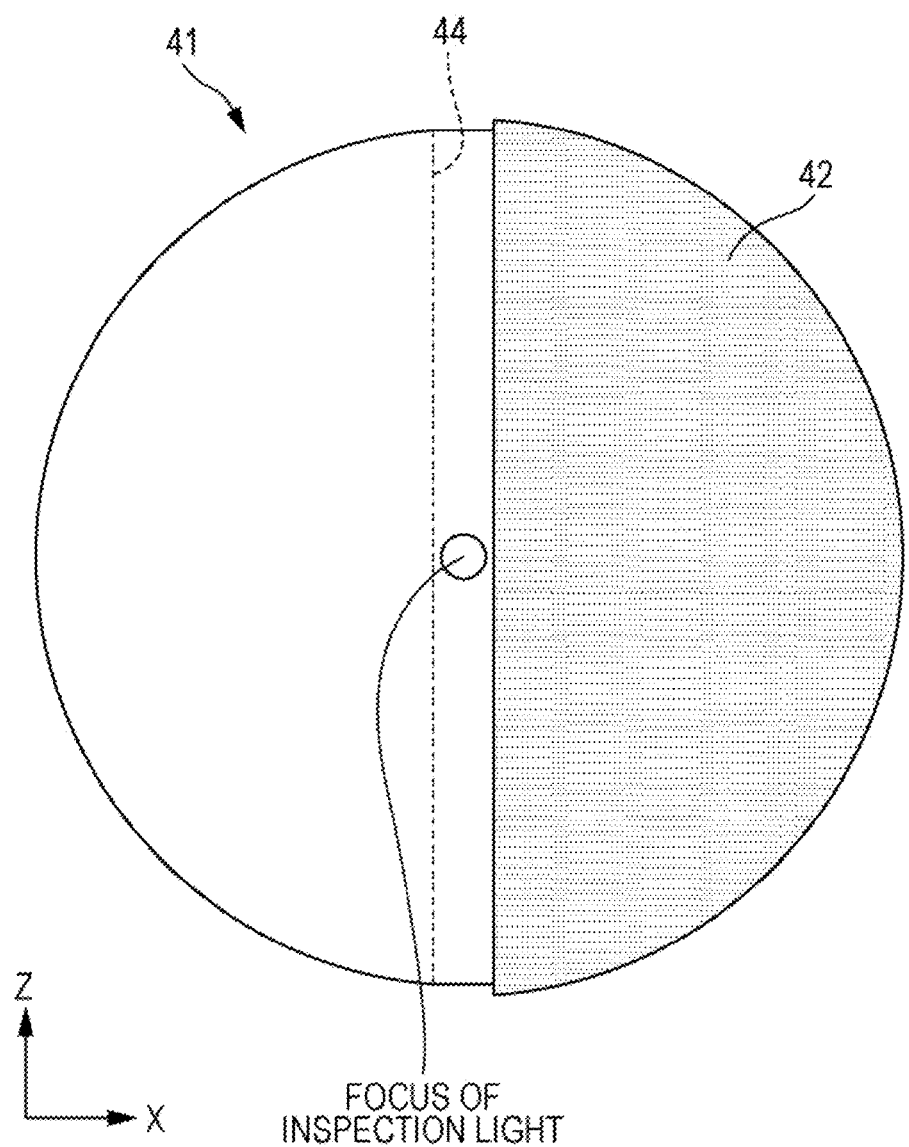
FIG. 9 is a schematic side view of a flow cell according to the fourth embodiment of the present disclosure.

A particle detector according to a fourth embodiment of the present disclosure includes, as illustrated in FIG. 8, the inspection light source 30, the flow cell 41, an elliptical mirror 50, and optical detectors 60A, 60B, and 60C. The inspection light source 30 emits the inspection light. The flow cell 41 allows the fluid containing the particles irradiated with the inspection light to flow therethrough and includes the semispherical reflective film 42 that reflects the reaction light generated by the particles irradiated with the inspection light. The elliptical mirror 50 has a first focus at the position of the flow cell 41 and reflects the reaction light having passed through the semispherical lens portion of the flow cell 41. The optical detectors 60A, 60B, and 60C are disposed at a second focus of the elliptical mirror 50 and detect the reaction light reflected by the elliptical mirror 50.

Figure 10:
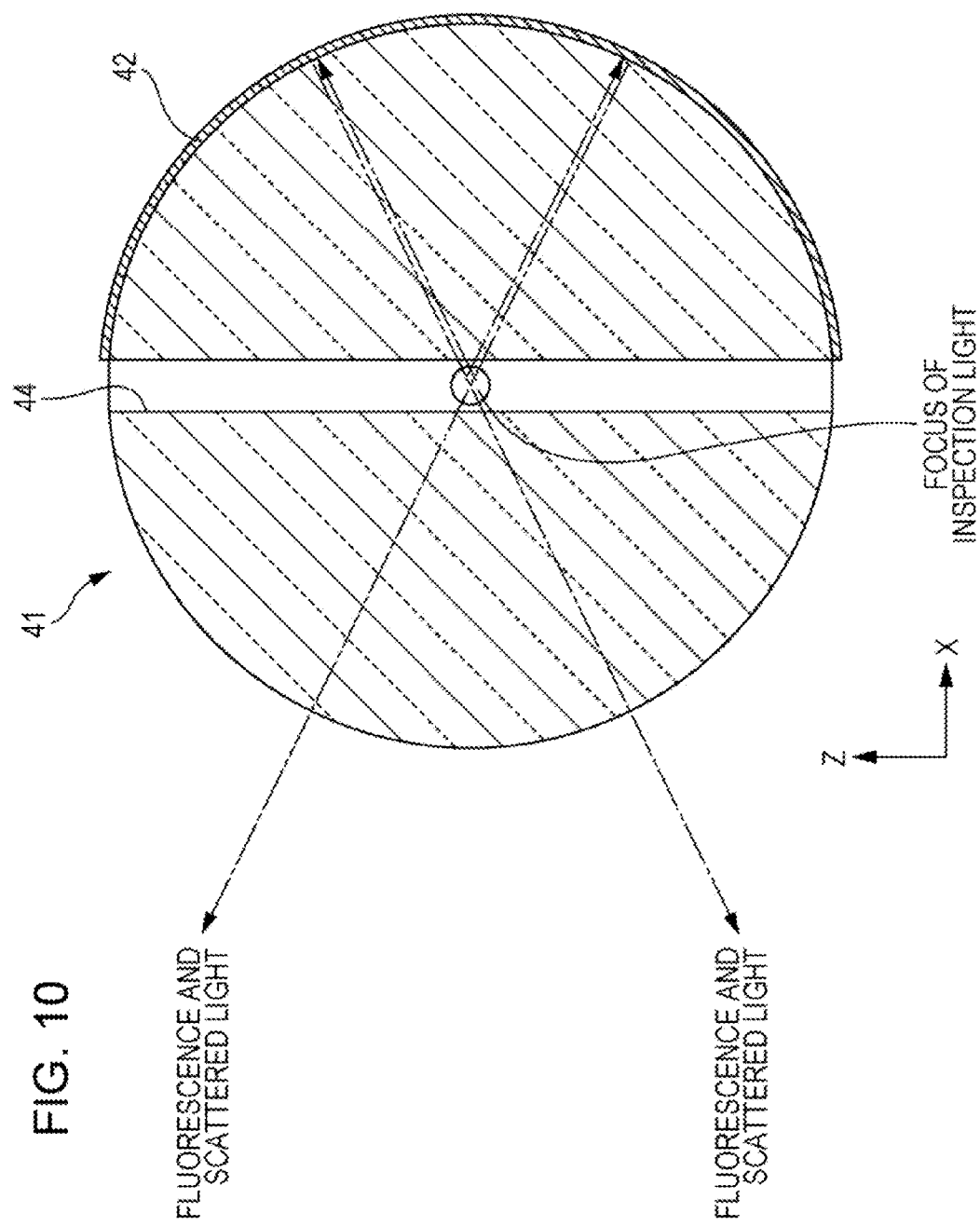
FIG. 10 is a schematic sectional view of the flow cell according to the fourth embodiment of the present disclosure.

The extending direction of the through hole 44 of the flow cell 41 is perpendicular to the traveling direction of the inspection light and perpendicular to a major axis direction of the elliptical mirror 50. As illustrated in FIGS. 3 and 10, the semispherical reflective film 42 covers part of the flow cell 41, for example, covers about a half of the flow cell 41 divided by the through hole 44. The part of the flow cell 41 not covered by the semispherical reflective film 42 functions as the semispherical lens portion.

As illustrated in FIG. 8, the flow cell 41 is disposed such that a convex portion of the semispherical lens portion and the concave portion of the semispherical reflective film 42 face the elliptical mirror 50. Furthermore, the flow cell 41 is disposed such that the center of the flow cell 41 where the through hole 44 passes is coincident with the first focus of the elliptical mirror 50.

The fluorescence and the scattered light having traveled toward the semispherical lens portion of the flow cell 41 illustrated in FIG. 10 exit through the surface of the semispherical lens portion and reach the elliptical mirror 50 illustrated in FIG. 8. In the case where the focus of the inspection light is coincident with the center of the spherical flow cell 41, the fluorescence and the scattered light generated at the focus of the inspection light perpendicularly or substantially perpendicularly exit through the surface of the semispherical lens portion of the flow cell 41.

The fluorescence and the scattered light having traveled toward the semispherical reflective film 42 of the flow cell 41 illustrated in FIG. 10 are reflected by the semispherical reflective film 42, exit through the surface of the semispherical lens portion, and reach the elliptical mirror 50 illustrated in FIG. 8. In the case where the focus of the inspection light is coincident with the center of the flow cell 41, the fluorescence and the scattered light generated at the focus of the inspection light are perpendicularly or substantially perpendicularly incident upon the semispherical reflective film 42 illustrated in FIG. 10. Thus, the fluorescence and the scattered light are perpendicularly or substantially perpendicularly reflected by the semispherical reflective film 42, pass through the center or the substantial center of the flow cell 41, and perpendicularly or substantially perpendicularly exit through the surface of the semispherical lens portion.

The concavity of the elliptical mirror 50 illustrated in FIG. 8 faces the concavity of the semispherical reflective film 42 and the convexity of the semispherical lens portion of the flow cell 41. The fluorescence and the scattered light having exited the flow cell 41 are reflected by the elliptical mirror 50 and condensed at the second focus of the elliptical mirror 50 behind the flow cell 41. For example, by sufficiently increasing the size of the elliptical mirror 50 compared to the semispherical reflective film 42 of the flow cell 41, efficiency with which the fluorescence and the scattered light are condensed by the elliptical mirror 50 is improved.

The elliptical mirror 50 has cuts 51 at portions thereof where the elliptical mirror 50 intersects the sector-shaped plane 200 that has the vertex at the intersection point of the inspection light and the through hole 44 of the flow cell 41, is parallel to the optical path of the inspection light, and is perpendicular to the extending direction of the through hole 44 of the flow cell 41. This can prevent the stray light from being reflected by the elliptical mirror 50 and reaching the optical detectors 60A, 60B, and 60C. Furthermore, a stray light attenuation member 80 that attenuates the stray light may be disposed in a traveling direction of the stray light. The stray light attenuation member 80 absorbs the stray light. Herein, the term "attenuation" means a 100% attenuation. In other words, the attenuation means blocking of the stray light.

Since the elliptical mirror 50 has the cuts 51, the elliptical mirror 50 does not reflect the stray light and the reaction light included in the sector-shaped plane 200 that has the vertex at the intersection point of the inspection light and the through hole 44 of the flow cell 41, is parallel to the optical path of the inspection light, and is perpendicular to the extending direction of the through hole 44 of the flow cell 41. The elliptical mirror 50 reflects the reaction light which exits the flow cell 41 so as to be angled relative to the sector-shaped plane 200. In other words, the elliptical mirror 50 reflects the reaction light having exited the flow cell 41 while not being included in the sector-shaped plane 200.

Wavelength selective reflectors 70A and 70B are disposed between the first and second geometrical foci of the elliptical mirror 50.

The wavelength selective reflector 70A wavelength selectively reflects, for example, the scattered light. The focus of the scattered light reflected by the wavelength selective reflector 70A is optically equivalent to the second geometrical focus of the elliptical mirror 50. The optical detector 60A that detects the scattered light is disposed at the focus of the scattered light reflected by the wavelength selective reflector 70A.

The wavelength selective reflector 70B, for example, wavelength selectively reflects the fluorescence of a first wavelength band and allows the fluorescence of a second wavelength band to pass therethrough. The focus of the fluorescence reflected by the wavelength selective reflector 70B is optically equivalent to the second geometrical focus of the elliptical mirror 50. The optical detector 60B that detects the fluorescence of the first wavelength band is disposed at the focus of the fluorescence of the first wavelength band reflected by the wavelength selective reflector 70B. The optical detector 60C that detects the fluorescence of the second wavelength band is disposed at the focus of the fluorescence of the second wavelength band having passed through the wavelength selective reflector 70B.

Any of a dichroic mirror, an interference film filter, an optical filter, and so forth may be used as the wavelength selective reflectors 70A and 70B. When the incident angles relative to the wavelength selective reflectors 70A and 70B are 45 degrees in the design, spectral efficiency of the interference film filters tends to increase by setting the distance between the first focus and the second focus of the elliptical mirror 50 so that the incident angles of the scattered light and the fluorescence relative to the wavelength selective reflectors 70A and 70B are from 35 to 55 degrees. However, this is not limiting.

With the above-described particle defector according to the fourth embodiment, the fluorescence and the scattered light having initially traveled to an opposite side to the elliptical mirror 50 can be condensed at the positions of the optical detectors 60A, 60B, and 60C by reflecting the fluorescence and the scattered light toward the elliptical mirror 50 by using the semispherical reflective film 42. Accordingly, the fluorescence and the scattered light that have been initially omnidirectionally emitted from the particles in the flow cell 41 can be condensed with efficiency equal to or higher than that of a lens condensing system and detected.

Furthermore, in the particle detector according to the fourth embodiment, the size of the semispherical reflective film 42 can be reduced by disposing the semispherical reflective film 42 in the flow cell 41. Accordingly, the area of the shadow of the semispherical reflective film 42 can be reduced and the efficiency with which the fluorescence and the scattered light are condensed is improved. Thus, the weak fluorescence and the scattered light can be efficiently detected without a complex optical system that includes an expensive high-numerical-aperture lens.

Variant of Fourth Embodiment

In the structure illustrated in FIG. 8, the elliptical mirror 50 has the cuts 51 at the portions thereof where the elliptical mirror 50 intersects the sector-shaped plane 200 which has the vertex at the intersection point of the inspection light and the through hole 44 of the flow cell 41, is parallel to the optical path of the inspection light, and is perpendicular to the extending direction of the through hole 44 of the flow cell 41. Alternatively, a band-shaped stray light attenuation member may be disposed at the portion of the elliptical mirror 50 where the elliptical mirror 50 intersects the sector-shaped plane 200. This can also prevent the stray light from being reflected by the elliptical mirror 50 and reaching the optical detectors 60A, 60B, and 60C.

Fifth Embodiment

Figure 11:
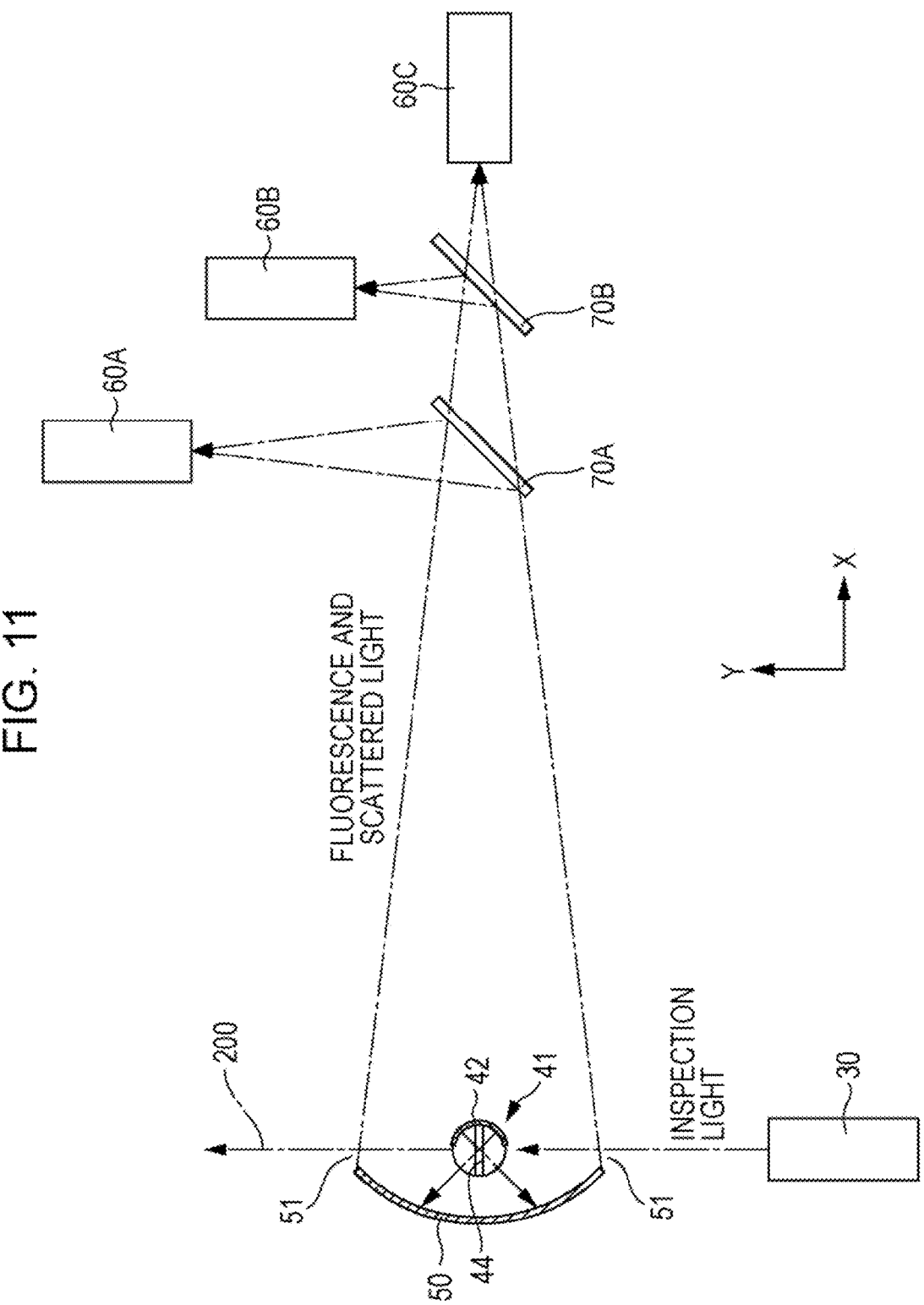
FIG. 11 is a schematic view of a particle detector according to a fifth embodiment of the present disclosure.

In an example of the fourth embodiment, as illustrated in FIG. 8, the extending direction of the through hole 44 of the flow cell 41 is perpendicular to the traveling direction of the inspection light and perpendicular to the major axis direction of the elliptical mirror 50. Alternatively, as illustrated in FIG. 11, the extending direction of the through hole 44 of the flow cell 41 may be perpendicular to the traveling direction of the inspection light and parallel to the major axis direction of the elliptical mirror 50.

Figure 12:
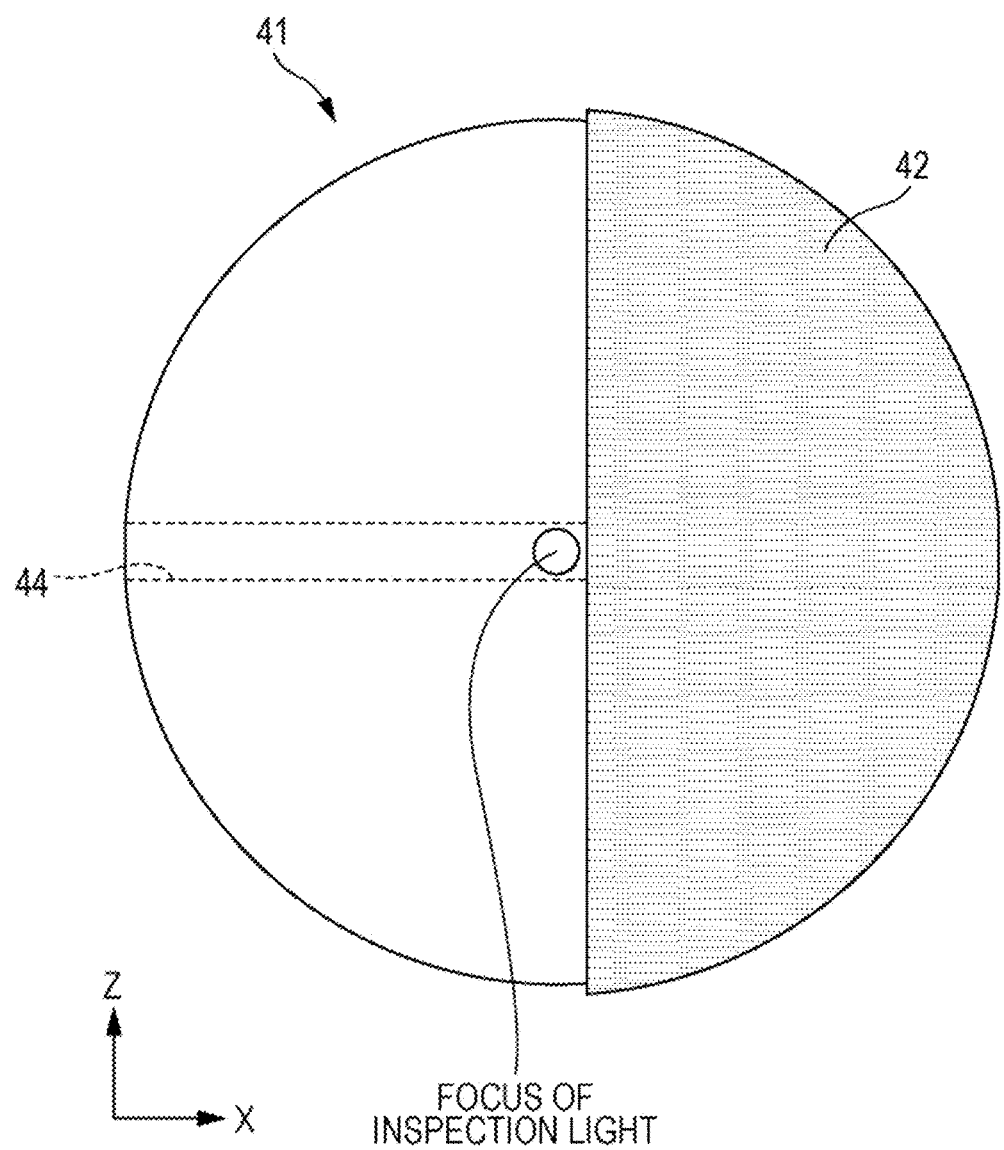
FIG. 12 is a schematic side view of a flow cell according to the fifth embodiment of the present disclosure.
Figure 13:
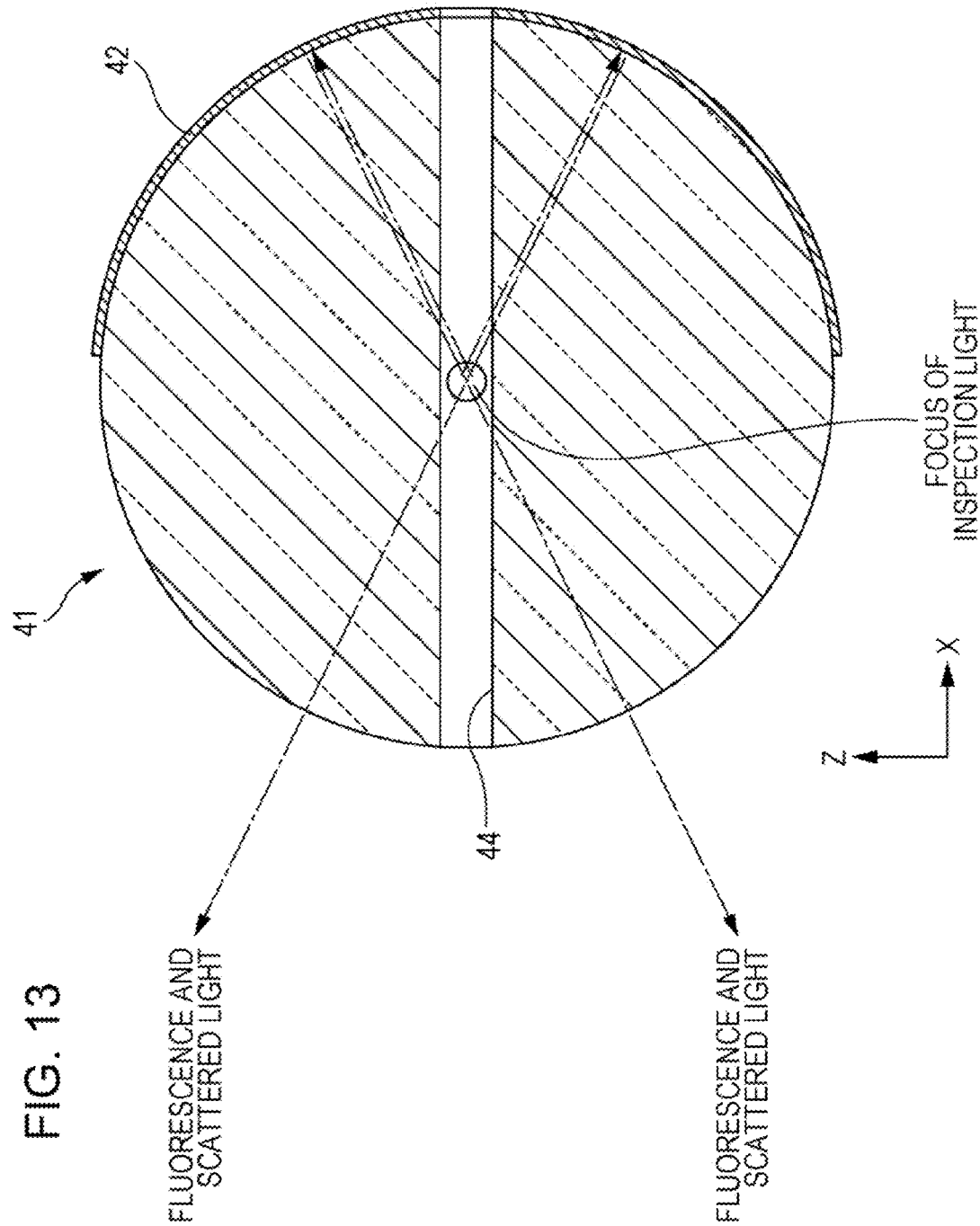
FIG. 13 is a schematic sectional view of the flow cell according to the fifth embodiment of the present disclosure.

According to a fifth embodiment, as illustrated in FIGS. 12 and 13, one of openings of the through hole 44 of the flow cell 41 is provided at the center of a portion covered by the semispherical reflective film 42, and another opening of the through hole 44 is provided at the center of a portion that is not covered by the semispherical reflective film 42 of the flow cell 41 and that functions as the semispherical lens portion.

Other elements of a particle detector according to the fifth embodiment are the same as or similar to those of the fourth embodiment. In the particle detector according to the fifth embodiment, the stray light is generated in a plane perpendicular to the through hole 44 of the flow cell 41 and the major axis of the elliptical mirror 50 illustrated in FIG. 11. Thus, entrance of the stray light toward a vertex side intersecting the major axis of the elliptical mirror 50 can be suppressed. Furthermore, the size of the cuts 51 provided in the elliptical mirror 50 can be reduced. Furthermore, the cuts 51 themselves are not necessarily provided when the elliptical mirror 50 does not intersects the sector-shaped plane 200 that has the vertex at the intersection point of the inspection light and the through hole 44 of the flow cell 41, is parallel to the optical path of the inspection light, and is perpendicular to the extending direction of the through hole 44 of the flow cell 41. Furthermore, since the through hole 44 of the flow cell 41 is coincident with the major axis of the elliptical mirror 50, an effect of shading a channel or the like connected to the through hole 44 from the fluorescence and the scattered light can be suppressed.

Sixth Embodiment

Figure 14:
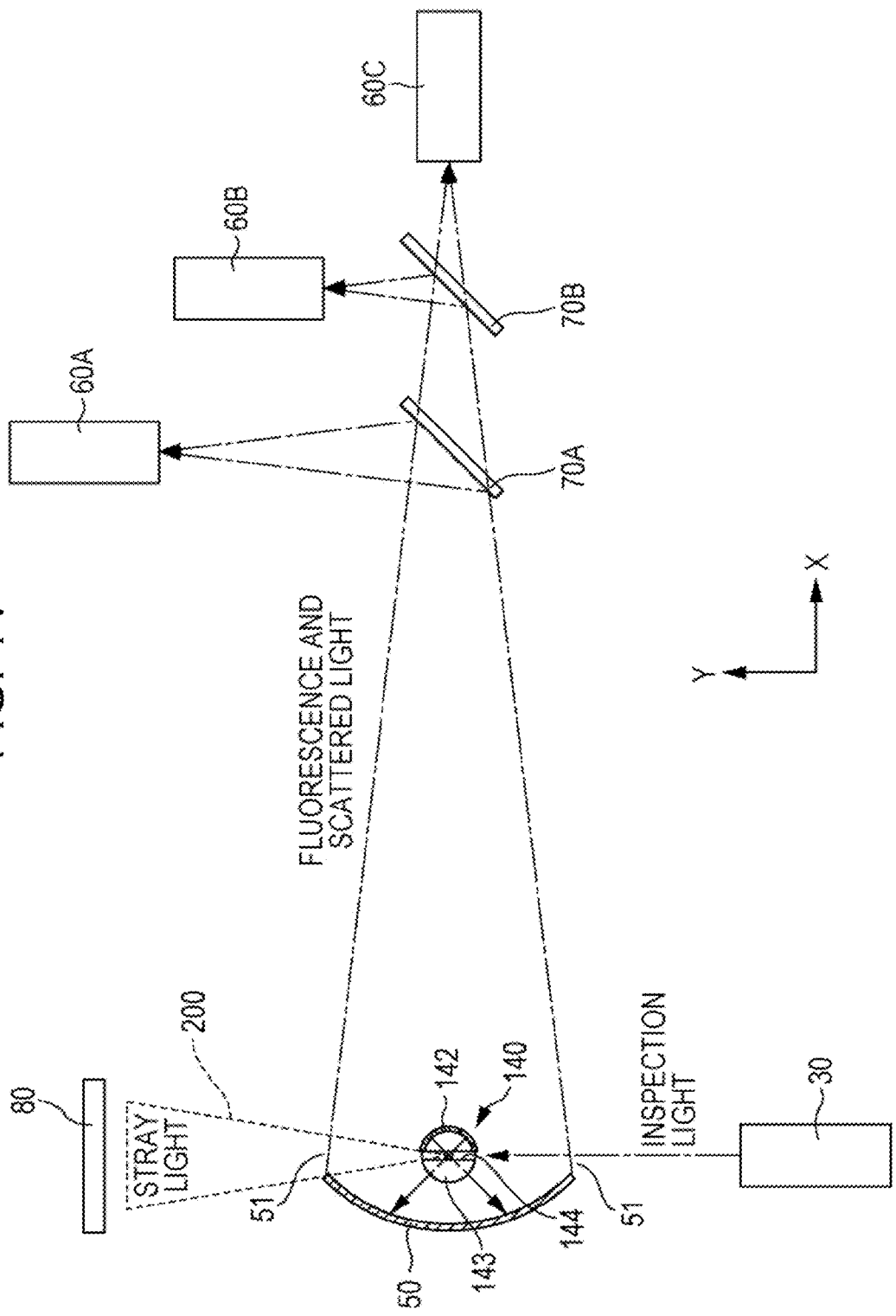
FIG. 14 is a schematic view of a particle detector according to a sixth embodiment of the present disclosure.
Figure 15:
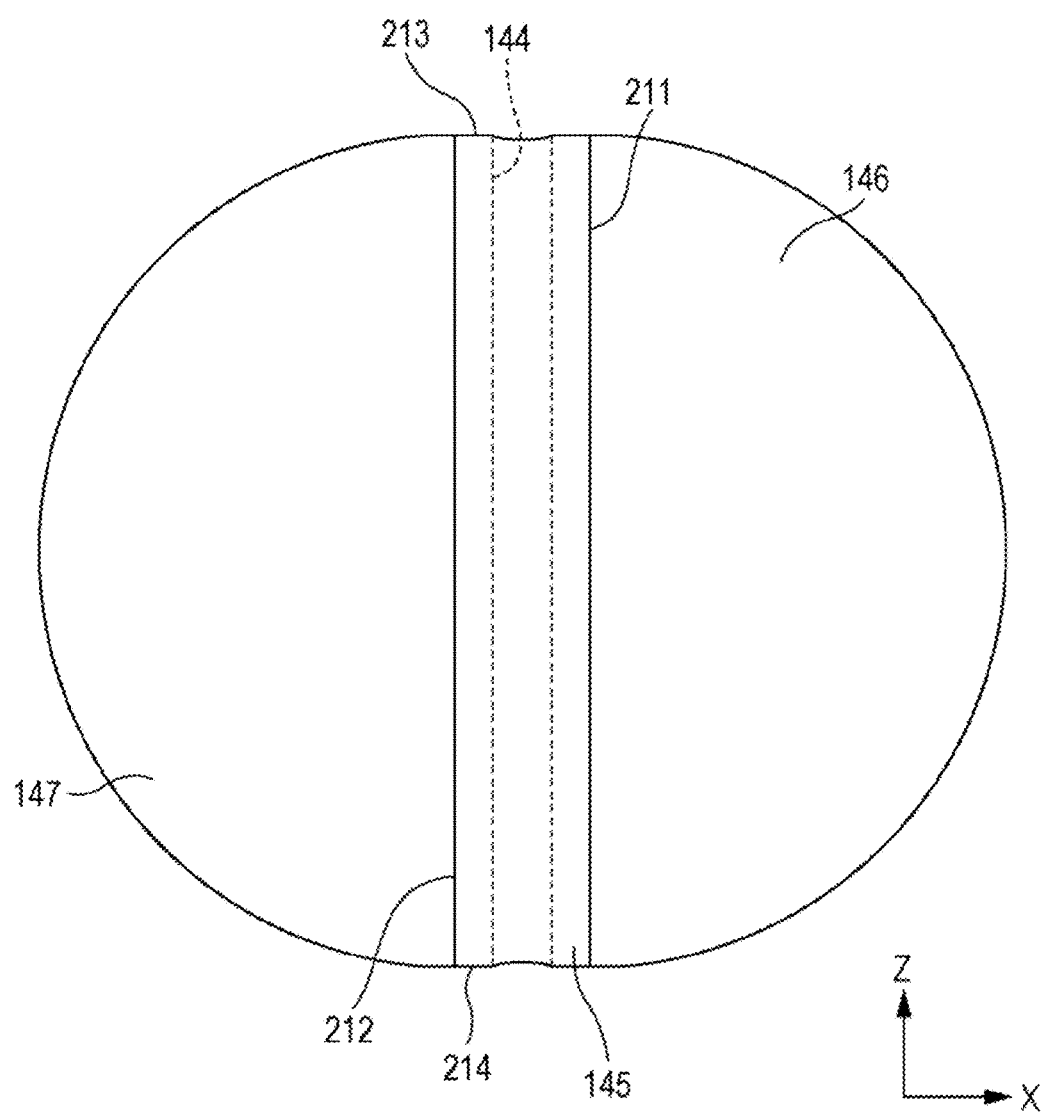
FIG. 15 is a schematic side view of a plate-shaped member, a first semispherical member, and a second semispherical member which are included in a flow cell according to the sixth embodiment of the present disclosure.

A flow cell 140 of a particle detector according to a sixth embodiment illustrated in FIG. 14 includes, as illustrated in FIG. 15, a plate-shaped member 145, a first semispherical member 146, and a second semispherical member 147. As illustrated in FIG. 15, the plate-shaped member 145 is transparent and includes a first main surface 211, a second main surface 212 that faces the first main surface 211, and side surfaces 213 and 214 that are perpendicular to the first and second main surfaces 211 and 212. The plate-shaped member 145 has a through hole 144 penetrating therethrough from the side surface 213 to the side surface 214. The first semispherical member 146 is transparent and disposed on the first main surface 211 of the plate-shaped member 145. The second semispherical member 147 is transparent and disposed on the second main surface 212 of the plate-shaped member 145.

Figure 16:
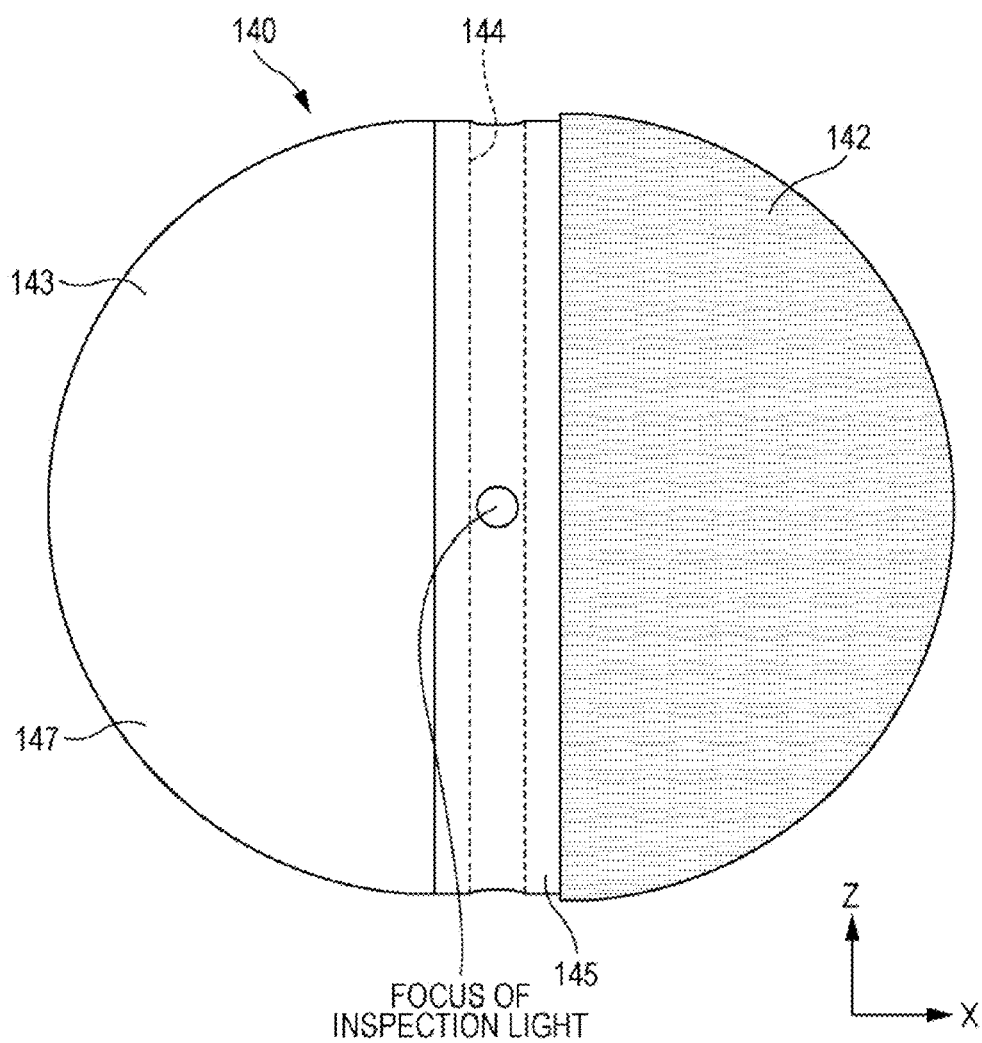
FIG. 16 is a schematic side view of the flow cell according to the sixth embodiment of the present disclosure.
Figure 17:
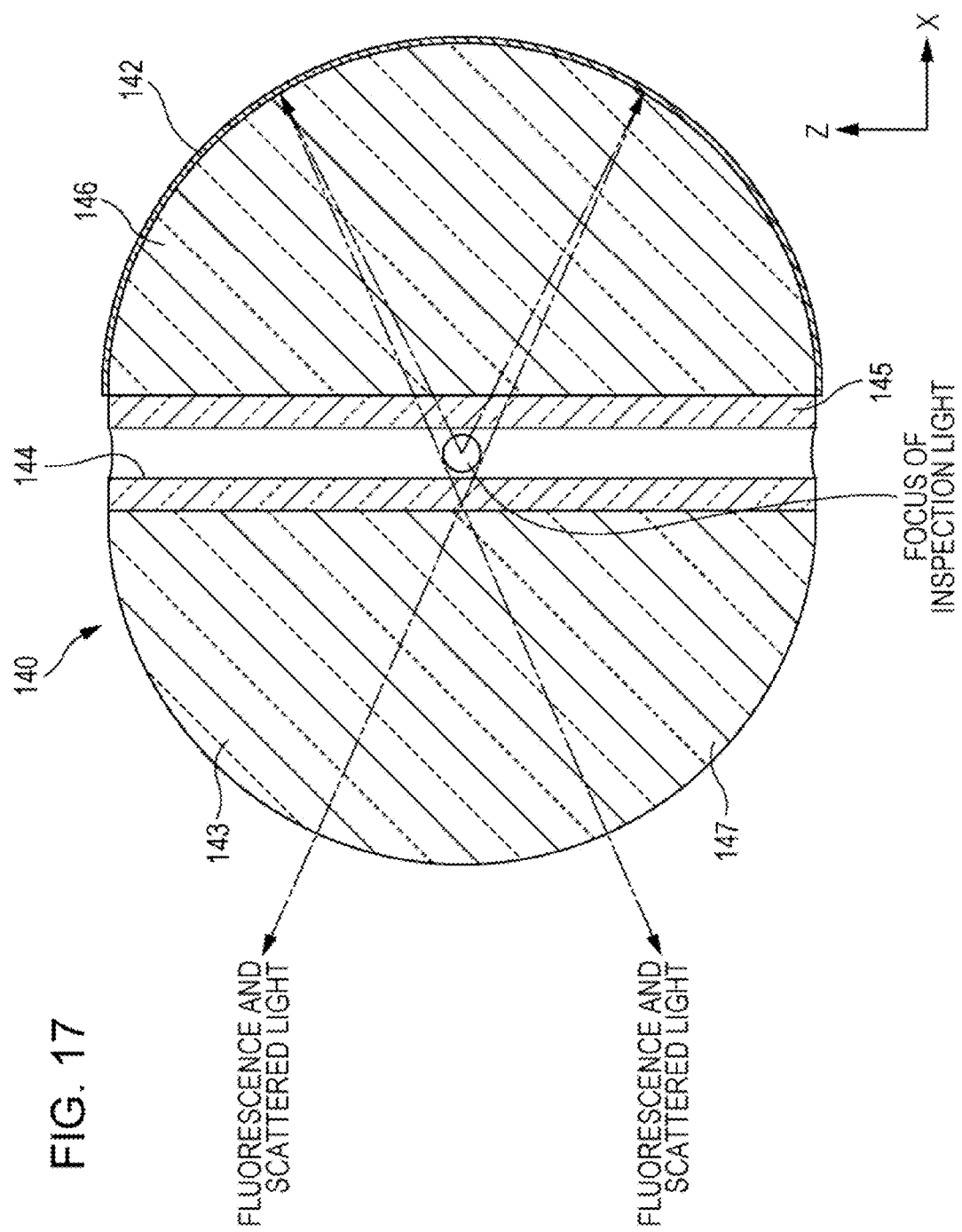
FIG. 17 is a schematic sectional view of the flow cell according to the sixth embodiment of the present disclosure.

As illustrated in FIGS. 15 to 17, in the flow cell 140, a semispherical reflective film 142 covers the first semispherical member 146, and the second semispherical member 147 functions as a semispherical lens portion 143. The semispherical reflective film 142 and the semispherical lens portion 143 face each other.

The first main surface 211 and the second main surface 212 of the plate-shaped member 145 each have, for example, a rectangular shape. The shapes of the first main surface 211 and the second main surface 212 may conform to the shape of a holder of the flow cell 140. The through hole 144 is perpendicular to the side surfaces 213 and 214 of the plate-shaped member 145. The through hole 144 passes through, for example, the center of the plate-shaped member 145 which is the center of the flow cell 140. The through hole 144 has a circular sectional shape when seen in the extending direction thereof. The extending direction of the through hole 144 illustrated in FIG. 14 is perpendicular to the traveling direction of the inspection light and perpendicular to the major axis direction of the elliptical mirror 50.

The excitation light as the inspection light for detecting the particles flowing through the flow cell 140 is incident upon, for example, a side surface perpendicular to the side surfaces 213 and 214 of the plate-shaped member 145 toward the through hole 144. Preferably, the side surface of the plate-shaped member 145 irradiated with the excitation light is ground so as to have a high smoothness.

The first and second semispherical members 146 and 147 illustrated in FIG. 15 each have a bottom surface and a spherical surface. The first and second semispherical members 146 and 147 can be two halves of a complete sphere. Alternatively, the first and second semispherical members 146 and 147 may be convex lens members the curvatures and the thicknesses of which are selected so that the reaction light generated at the intersection point of the inspection light and the through hole 144 is perpendicularly incident upon the surfaces of the first and second semispherical members 146 and 147. Outer diameters of the bottom surfaces of the first and second semispherical members 146 and 147 are, for example, the same as the widths of the first main surface 211 and the second main surface 212 of the plate-shaped member 145.

As illustrated in FIG. 17, the fluorescence and the scattered light generated by fluorescent particles that are irradiated with the excitation light in the through hole 144 are omnidirectionally emitted from the fluorescent particles. Here, the fluorescence and the scattered light having traveled toward the semispherical lens portion 143 of the flow cell 140 exit through a surface of the semispherical lens portion 143 and reach the elliptical mirror 50 illustrated in FIG. 14. In the flow cell 140 illustrated in FIG. 17, when the thickness of the plate-shaped member 145 is less than the thickness of the semispherical lens portion 143, the shape of the flow cell 140 approximates a spherical shape. Thus, in the case where the focus of the inspection light is coincident with the center of the flow cell 140, the fluorescence and the scattered light generated at the focus of the inspection light are perpendicularly or substantially perpendicularly incident upon the surface of the semispherical lens portion 143. Thus, the fluorescence and the scattered light exit through the surface of the semispherical lens portion 143 without or substantially without being refracted at the surface of the semispherical lens portion 143.

The fluorescence and the scattered light having traveled toward the semispherical reflective film 142 of the flow cell 140 are reflected by the semispherical reflective film 142, exit through the surface of the semispherical lens portion 143, and reach the elliptical mirror 50 illustrated in FIG. 14. In the case where the shape of the flow cell 140 can approximate the spherical shape and the focus of the inspection light is coincident with the center of the flow cell 140, the fluorescence and the scattered light generated at the focus of the inspection light are perpendicularly or substantially perpendicularly incident upon the semispherical reflective film 142 illustrated in FIG. 17. Thus, the fluorescence and the scattered light are perpendicularly or substantially perpendicularly reflected by the semispherical reflective film 142, pass through the center or a portion near the center of the flow cell 140, and exit through the surface of the semispherical lens portion 143 without or substantially without being refracted at the surface of the semispherical lens portion 143.

Also according to the sixth embodiment, since the elliptical mirror 50 illustrated in FIG. 14 has the cuts 51, the elliptical mirror 50 does not reflect the stray light and the reaction light included in the sector-shaped plane 200 that has the vertex at the intersection point of the inspection light and the through hole 144 of the flow cell 140, is parallel to the optical path of the inspection light, and is perpendicular to the extending direction of the through hole 144 of the flow cell 140. The elliptical mirror 50 reflects the reaction light which exits the flow cell 140 so as to be angled relative to the sector-shaped plane 200. In other words, the elliptical mirror 50 reflects the reaction light having exited the flow cell 140 while not being included in the sector-shaped plane 200.

The light intensity of the inspection light passing through the plate-shaped member 145 is higher than the light intensities of the fluorescence and the scattered light generated by the particles in the through hole 144, The excitation light, which has a high light intensity, may cause the stray light. Thus, the plate-shaped member 145 upon which the inspection light is incident is preferably formed of a material having a high transparency such as synthetic quartz. In contrast, the fluorescence and the scattered light, which have low light intensities, are unlikely to cause the stray light. Thus, although the transparencies of the materials of the first and second semispherical members 146 and 147 may be the same as the transparency of the material of the plate-shaped member 145, the first and second semispherical members 146 and 147 may alternatively be formed of cheap materials having lower transparencies than the transparency of the material of the plate-shaped member 145 as long as the first and second semispherical members 146 and 147 allow the fluorescence and the scattered light to pass therethrough.

Specifically, the first and second semispherical members 146 and 147 may be formed of a silica glass. Alternatively, the first and second semispherical members 146 and 147 may be formed of a different optical glass from silica glass or transparent resin such as polymethyl methacrylate (PMMA).

Other elements of the particle detector according to the sixth embodiment are the same as or similar to those of the fourth embodiment. Also with the particle detector according to the sixth embodiment, the reaction light such as fluorescence and scattered light generated in the flow cell 140 can be efficiently condensed and detected.

Seventh Embodiment

Figure 18:
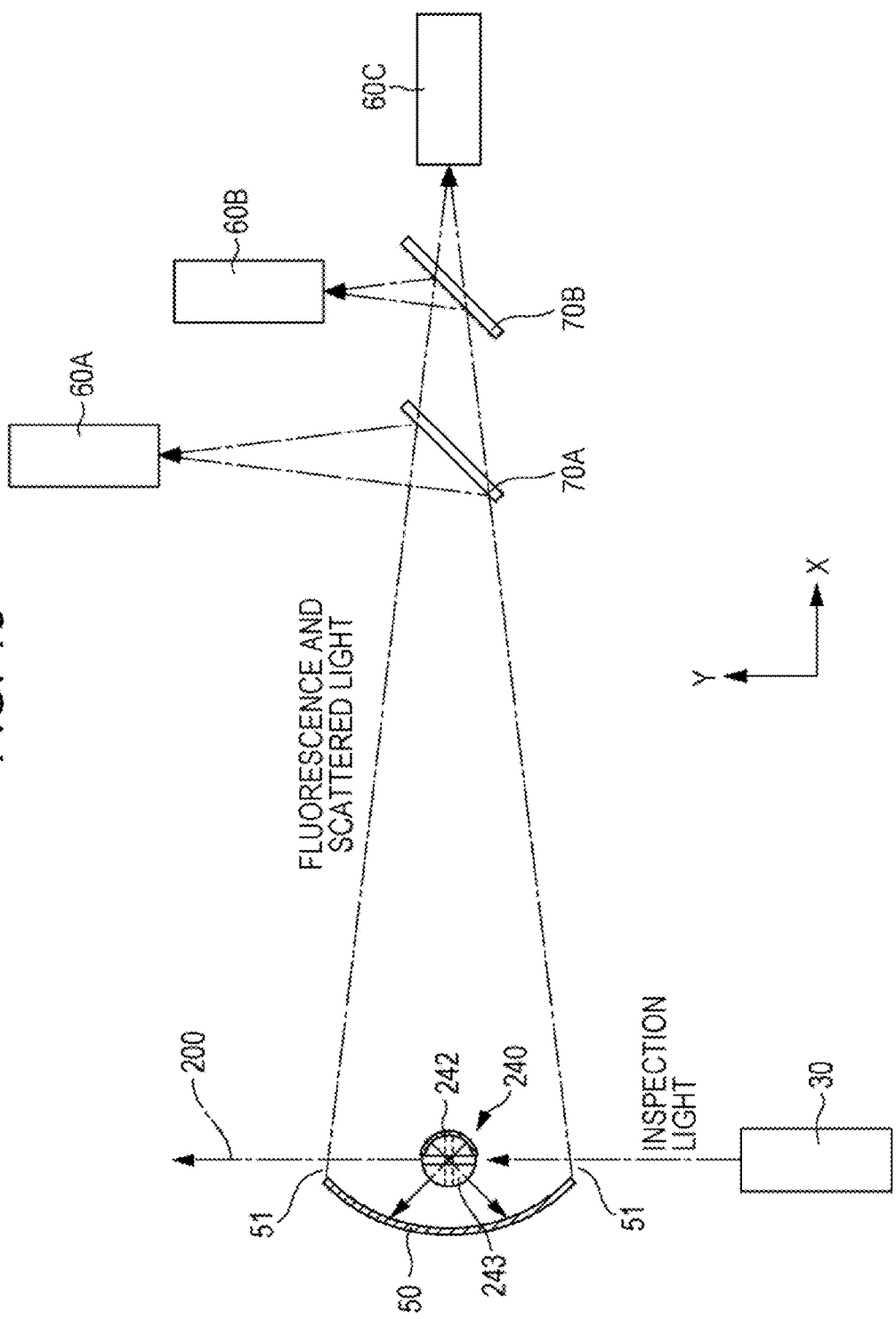
FIG. 18 is a schematic view of a particle detector according to a seventh embodiment of the present disclosure.
Figure 19:
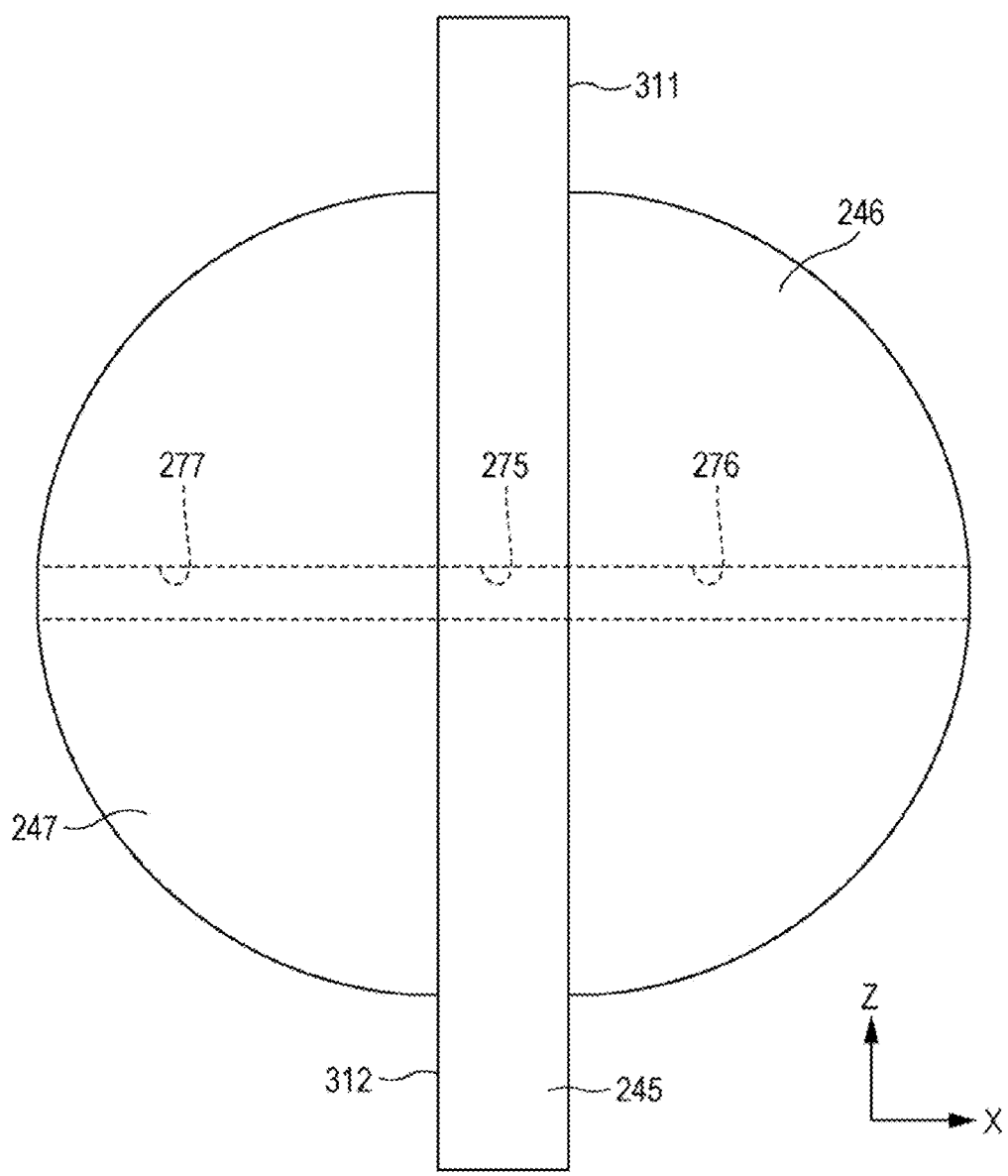
FIG. 19 is a schematic side view of a plate-shaped member, a first semispherical member, and a second semispherical member which are included in a flow cell according to the seventh embodiment of the present disclosure.
Figure 20:
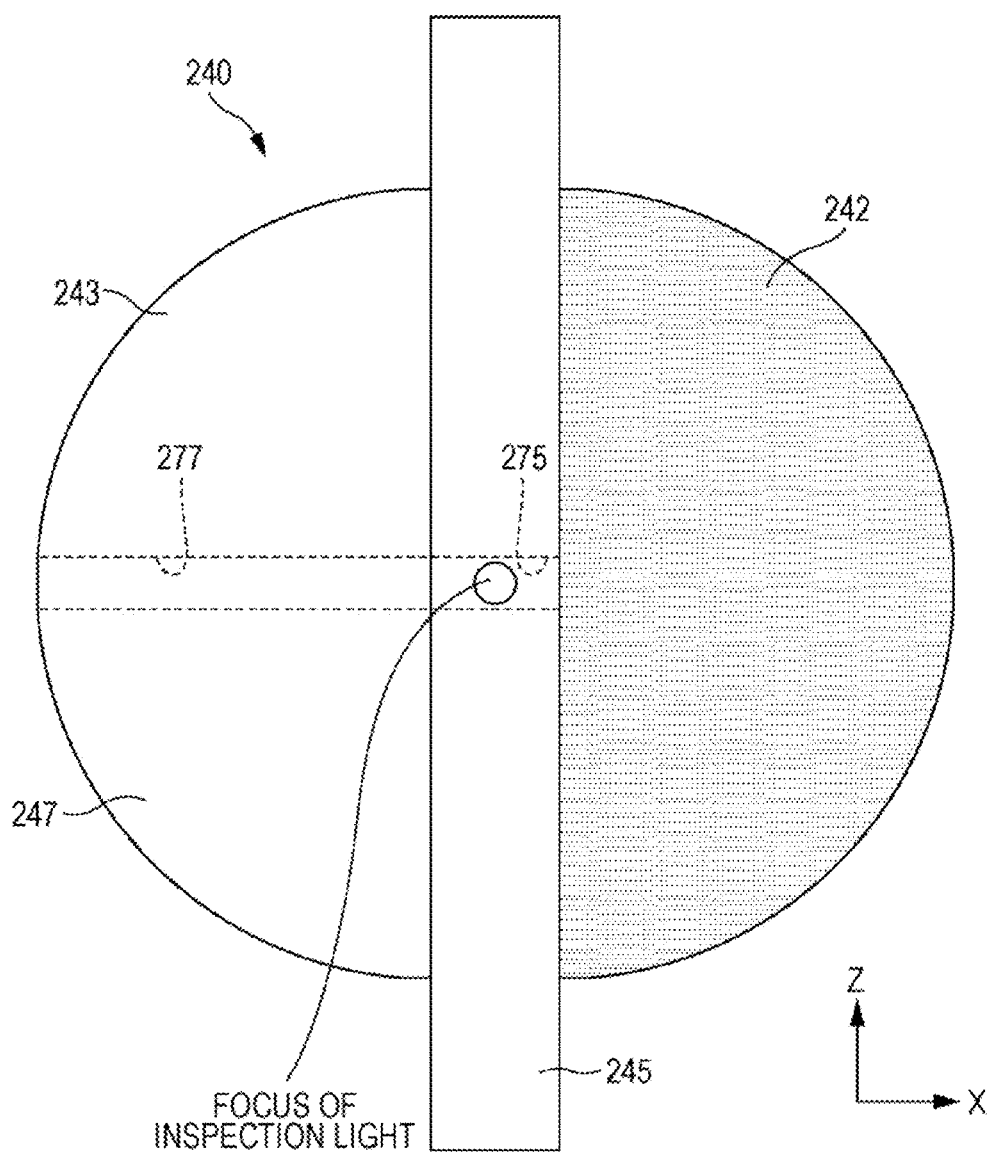
FIG. 20 is a schematic side view of the flow cell according to the seventh embodiment of the present disclosure.

A flow cell 240 of a particle detector according to a seventh embodiment illustrated in FIG. 18 includes, as illustrated in FIG. 19, a plate-shaped member 245, a first semispherical member 246, and a second semispherical member 247. As illustrated in FIG. 19, the plate-shaped member 245 is transparent, includes a first main surface 311, a second main surface 312 that faces the first main surface 311, and includes a through hole 275 penetrating therethrough from the first main surface 311 to the second main surface 312. The first semispherical member 246 is transparent, has a through hole 276, and is disposed on the first main surface 311 of the plate-shaped member 245 such that the through hole 275 of the plate-shaped member 245 and the through hole 276 of the first semispherical member 246 communicate with each other. The second semispherical member 247 is transparent, has a through hole 277, and is disposed on the second main surface 312 of the plate-shaped member 245 such that the through hole 275 of the plate-shaped member 245 and the through hole 277 of the second semispherical member 247 communicate with each other.

As illustrated in FIGS. 19 to 24, in the flow cell 240, a semispherical reflective film 242 covers the first semispherical member 246, and the second semispherical member 247 functions as a semispherical lens portion 243. The semispherical reflective film 242 and the semispherical lens portion 243 face each other.

The first main surface 311 and the second main surface 312 of the plate-shaped member 245 each have, for example, a rectangular shape. The shapes of the first main surface 311 and the second main surface 312 may conform to the shape of a holder of the flow cell 240. The through hole 275 is perpendicular to the first and second main surfaces 311 and 312. The plate-shaped member 245 is formed of, for example, silica glass. Preferably, a side surface of the plate-shaped member 245 irradiated with the excitation light is ground so as to have a high smoothness.

The through hole 275 provided in the plate-shaped member 245 passes through, for example, the center of the plate-shaped member 245 which is the center of the flow cell 240. The through hole 275 has a circular sectional shape when seen in the extending direction thereof. The extending direction of the through hole 275 is perpendicular to the traveling direction of the inspection light and parallel to the major axis direction of the elliptical mirror 50.

The first and second semispherical members 246 and 247 each have a bottom surface and a spherical surface. The first and second semispherical members 246 and 247 can be two halves of a complete sphere. Alternatively, the first and second semispherical members 246 and 247 may be convex lens members the curvatures and the thicknesses of which are selected so that the reaction light generated at the intersection point of the inspection light and the through hole 275 is perpendicularly incident upon the surfaces of the first and second semispherical members 246 and 247. Outer diameters of the bottom surfaces of the first and second semispherical members 246 and 247 may be the same as or smaller than the widths of the first main surface 311 and the second main surface 312 of the plate-shaped member 245. The through hole 276 of the first semispherical member 246 is perpendicularly provided from the top to the bottom of the first semispherical member 246. The through hole 276 has a circular sectional shape when seen in the extending direction thereof. The through hole 277 of the second semispherical member 247 is also perpendicularly provided from the top to the bottom of the second semispherical member 247. The through hole 277 has a circular sectional shape when seen in the extending direction thereof. The first and second semispherical members 246 and 247 are formed of, for example, silica glass. Alternatively, the first and second semispherical members 246 and 247 may be formed of, for example, a different optical glass from silica glass or transparent resin such as PMMA.

In the flow cell 240, the fluid flows through the through hole 276 of the first semispherical member 246, the through hole 275 of the plate-shaped member 245, and the through hole 277 of the second semispherical member 247. The fluid may flow from the first semispherical member 246 side to the second semispherical member 247 side or from the second semispherical member 247 side to the first semispherical member 246 side.

The excitation light as the inspection light for detecting the particles flowing through the flow cell 240 is incident upon, for example, the side surface perpendicular to the first and second main surfaces 311 and 312 of the plate-shaped member 245 toward the through hole 275. The fluorescence and the scattered light generated by the fluorescent particles that are irradiated with the excitation light in the through hole 275 are omnidirectionally emitted from the fluorescent particles.

Figure 21:
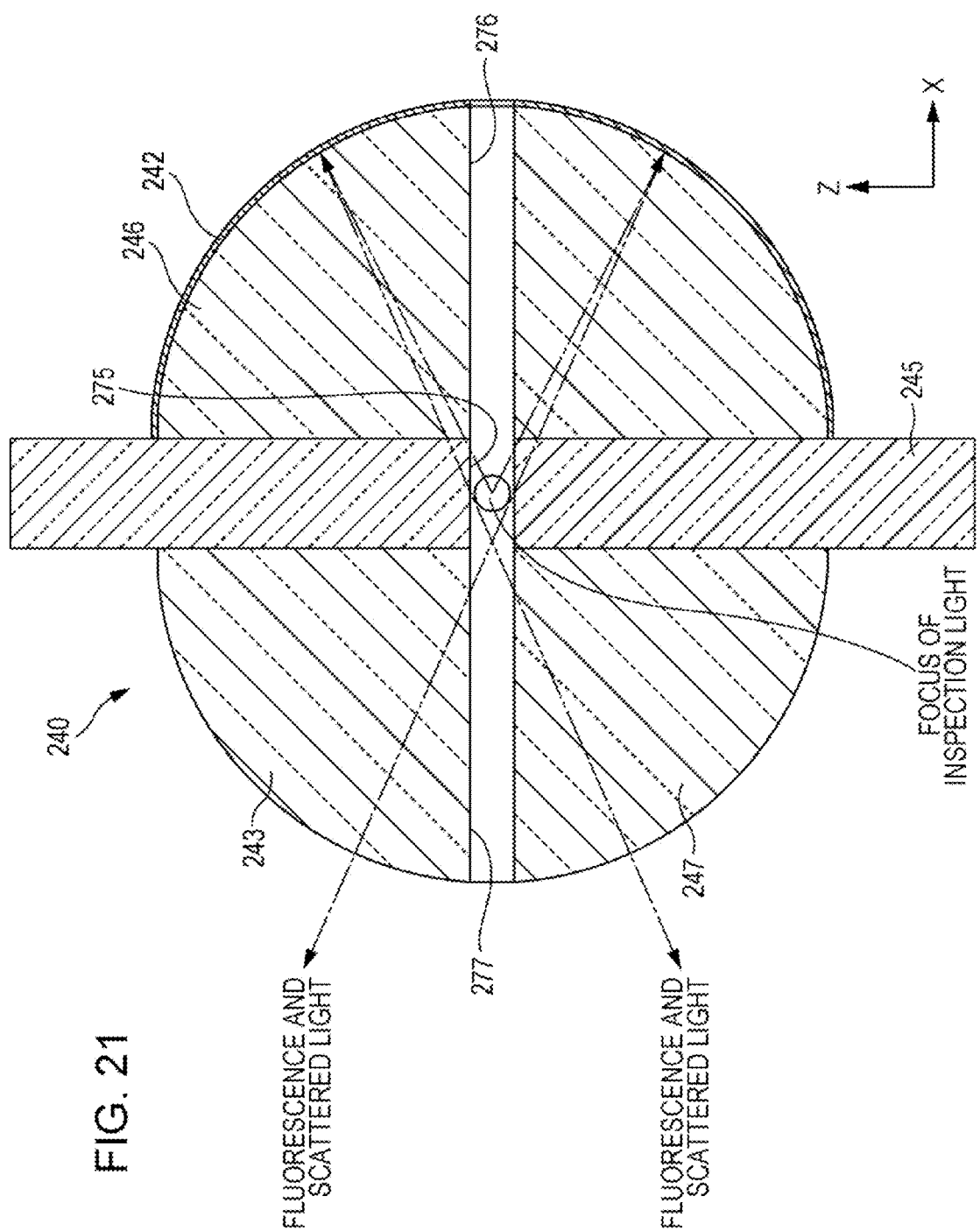
FIG. 21 is a schematic sectional view of the flow cell according to the seventh embodiment of the present disclosure.
Figure 22:
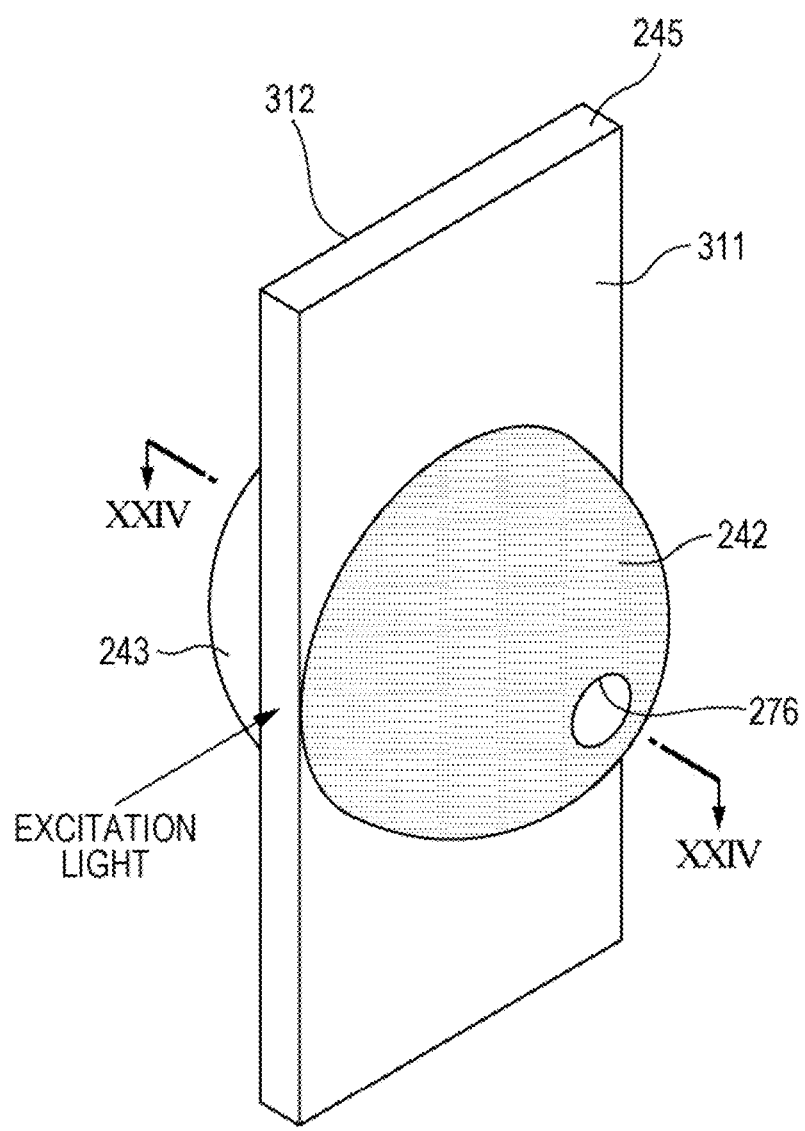
FIG. 22 is a schematic perspective view of the flow cell according to the seventh embodiment of the present disclosure.

The fluorescence and the scattered light having traveled toward the semispherical lens portion 243 of the flow cell 240 illustrated in FIG. 21 exit through the surface of the semispherical lens portion 243 and reach the elliptical mirror 50 illustrated in FIG. 18. In the flow cell 240, when the thickness of the plate-shaped member 245 illustrated in FIG. 21 is less than the thickness of the semispherical lens portion 243, the shape of the flow cell 240 approximates a spherical shape. Thus, in the case where the focus of the inspection light is coincident with the center of the flow cell 240, the fluorescence and the scattered light generated at the focus of the inspection light are perpendicularly or substantially perpendicularly incident upon the surface of the semispherical lens portion 243. Thus, the fluorescence and the scattered light exit through the surface of the semispherical lens portion 243 without or substantially without being refracted at the surface of the semispherical lens portion 243.

The fluorescence and the scattered light having traveled toward the semispherical reflective film 242 of the flow cell 240 are reflected by the semispherical reflective film 242, exit through the surface of the semispherical lens portion 243, and reach the elliptical mirror 50 illustrated in FIG. 18. In the case where the shape of the flow cell 240 can approximate the spherical shape and the focus of the inspection light is coincident with the center of the flow cell 240, the fluorescence and the scattered light generated at the focus of the inspection light are perpendicularly or substantially perpendicularly incident upon the semispherical reflective film 242 illustrated in FIG. 21. Thus, the fluorescence and the scattered light are perpendicularly or substantially perpendicularly reflected by the semispherical reflective film 242, pass through the center or a portion near the center of the flow cell 240, and exit through the surface of the semispherical lens portion 243 without or substantially without being refracted at the surface of the semispherical lens portion 243.

Other elements of the particle detector according to the seventh embodiment are the same as or similar to those of the fifth embodiment. Also in the particle detector according to the seventh embodiment, the stray light is generated in a plane perpendicular to the through holes of the flow cell 240 and the major axis of the elliptical mirror 50 illustrated in FIG. 18. Thus, entrance of the stray light toward a vertex side intersecting the major axis of the elliptical mirror 50 can be suppressed. Furthermore, the size of the cuts 51 provided in the elliptical mirror 50 can be reduced.

The through holes 276 and 277 of the first and second semispherical members 246 and 247 are not irradiated with the excitation light. Accordingly, the smoothness of inner walls of the through holes 276 and 277 of the first and second semispherical members 246 and 247 may be the same as the smoothness of an inner wall of the through hole 275 of the plate-shaped member 245 or may be lower than the smoothness of the inner wall of the through hole 275 of the plate-shaped member 245.

Furthermore, as the diameter of the through hole 275 of the plate-shaped member 245 reduces, a region from the focus of the inspection light in which inspection object substances flows reduces and the likelihood of a plurality of inspection object substances simultaneously passing through the focus of the inspection light reduces. Thus, as the diameter of the through hole 275 reduces, resolution for detecting the fluorescence and the scattered light tends to be improved. In contrast, the diameters of the through holes 276 and 277 of the first and second semispherical members 246 and 247 not irradiated with the excitation light produce a small effect on the resolution for detecting the fluorescence and the scattered light. Accordingly, the diameters of the through holes 276 and 277 of the first and second semispherical members 246 and 247 may be the same as the diameter of the through hole 275 of the plate-shaped member 245 or may be larger than the diameter of the through hole 275 of the plate-shaped member 245.

Furthermore, the light intensity of the inspection light passing through the plate-shaped member 245 is higher than the light intensities of the fluorescence and the scattered light generated by the particles in the through hole 275. The excitation light, which has a high light intensity, may cause the stray light. Thus, the plate-shaped member 245 upon which the inspection light is incident is preferably formed of a material having a high transparency such as synthetic quartz. In contrast, the fluorescence and the scattered light, which have low light intensities, are unlikely to cause the stray light. Thus, although the transparencies of the materials of the first and second semispherical members 246 and 247 may be the same as the transparency of the material of the plate-shaped member 245, the first and second semispherical members 246 and 247 may alternatively be formed of cheap materials having lower transparencies than the transparency of the material of the plate-shaped member 245 as long as the first and second semispherical members 246 and 247 allow the fluorescence and the scattered light to pass therethrough.

Figure 25:
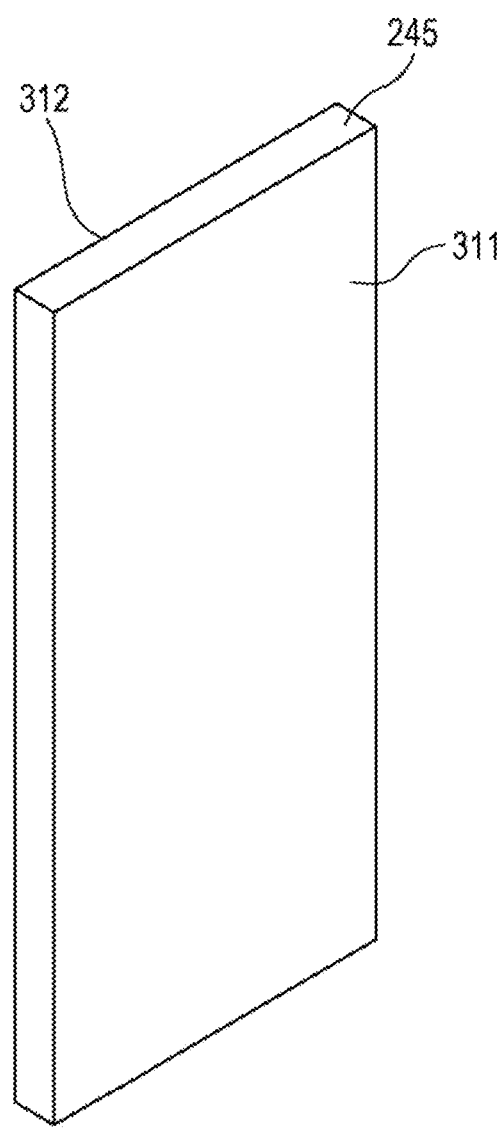
FIG. 25 is a view of a step illustrating a method of producing the flow cell according to the seventh embodiment of the present disclosure.
Figure 26:
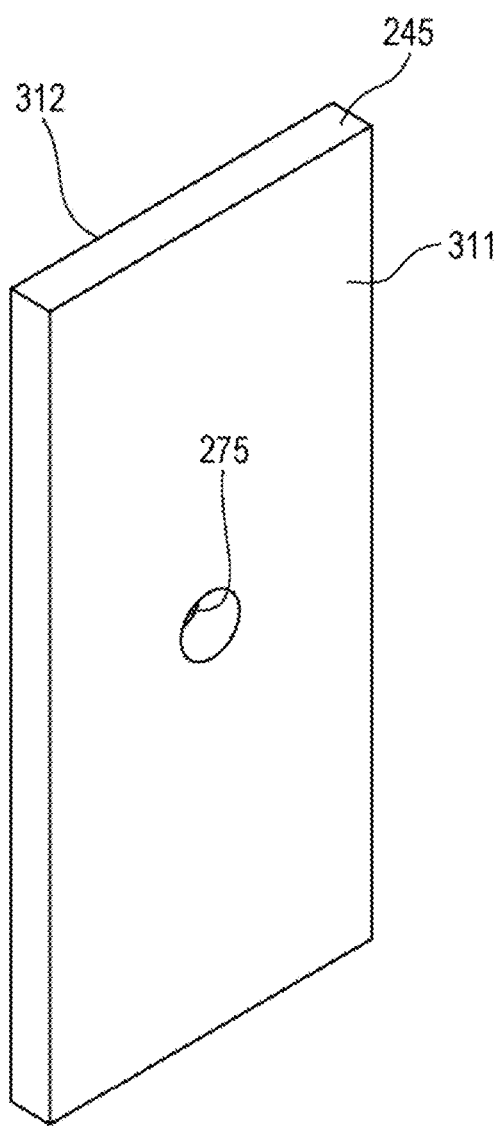
FIG. 26 is a view of a step illustrating the method of producing the flow cell according to the seventh embodiment of the present disclosure.
Figure 27:
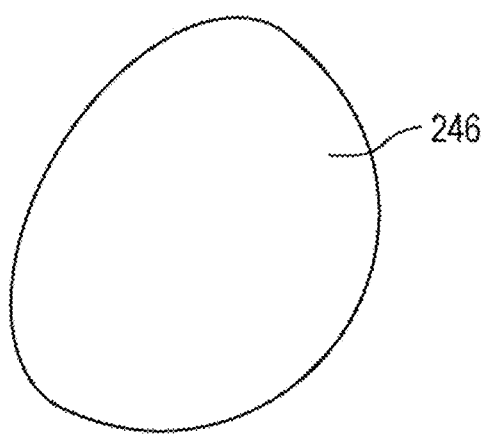
FIG. 27 is a view of a step illustrating the method of producing the flow cell according to the seventh embodiment of the present disclosure.
Figure 28:
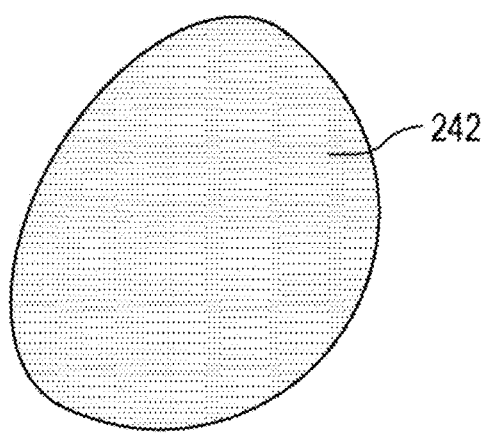
FIG. 28 is a view of a step illustrating the method of producing the flow cell according to the seventh embodiment of the present disclosure.
Figure 29:
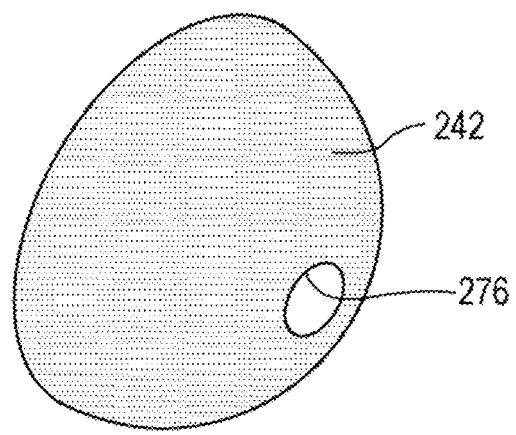
FIG. 29 is a view of a step illustrating the method of producing the flow cell according to the seventh embodiment of the present disclosure.
Figure 30:
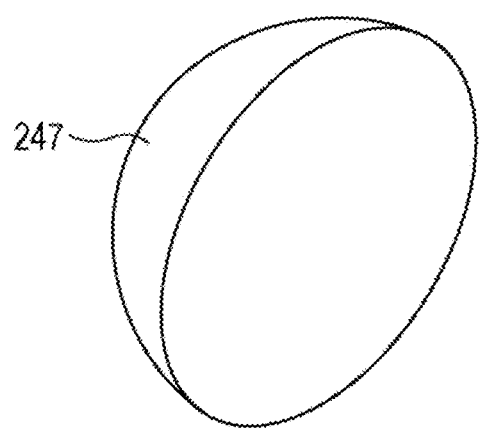
FIG. 30 is a view of a step illustrating the method of producing the flow cell according to the seventh embodiment of the present disclosure.
Figure 31:
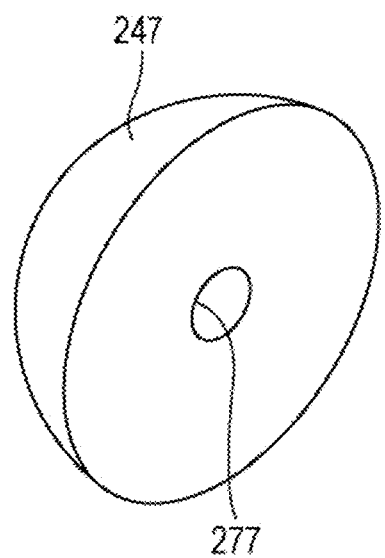
FIG. 31 is a view of a step illustrating the method of producing the flow cell according to the seventh embodiment of the present disclosure.

Next, a method of producing the flow cell 240 according to the seventh embodiment is described. The plate-shaped member 245 is prepared as illustrated in FIG. 25, and the through hole 275 is provided in the plate-shaped member 245 as illustrated in FIG. 26. Furthermore, the first semispherical member 246 is prepared as illustrated in FIG. 27, and the semispherical reflective film 242 is formed on the semispherical surface of the first semispherical member 246 as illustrated in FIG. 28. Furthermore, as illustrated in FIG. 29, the through hole 276 is provided in the first semispherical member 246 on which the semispherical reflective film 242 has been provided. Furthermore, the second semispherical member 247 is prepared as illustrated in FIG. 30, and the through hole 277 is provided in the second semispherical member 247 as illustrated in FIG. 31.

The through holes 275, 276, and 277 can be provided by, for example, etching. Alternatively, the through holes 275, 276, and 277 may be provided by drilling. Furthermore, after the through holes 275, 276, and 277 have been formed, the inner walls of the through holes 275, 276, and 277 may be, for example, ground so as to improve the smoothness of the inner walls of the through holes 275, 276 and 277. Alternatively, the inner wall of only the through hole 275 may be, for example, ground so as to improve the smoothness of the inner wall of the through hole 275.

Here, a through hole having a highly smooth inner wall can be easily provided in the plate-shaped member than in the semispherical members. Furthermore, as has been described, in the flow cell 240 to be produced, the plate-shaped member 245 is irradiated with the excitation light and the first and second semispherical members 246 and 247 are not irradiated with the excitation light. Accordingly, the production cost of the flow cell 240 according to the seventh embodiment may be reduced by providing the through hole 275 having a highly smooth inner wall in the plate-shaped member 245, and providing the through holes 276 and 277 having inner walls having lower smoothness than the smoothness of the inner wall of the through hole 275 in the first and second semispherical members 246 and 247.

Furthermore, a through hole having a small diameter can be easily provided in the plate-shaped member than in the semispherical members. Furthermore, as has been described, as the diameter of the through hole 275 of the plate-shaped member 245 reduces, the resolution for detecting the fluorescence and the scattered light is improved with the flow cell 240 to be produced. However, the diameters of the through holes 276 and 277 of the first and second semispherical members 246 and 247 not irradiated with the excitation light produce a small effect on the resolution for detecting the fluorescence and the scattered light. Accordingly, the production cost of the flow cell 240 according to the seventh embodiment may be reduced by providing the through hole 275 having a small diameter in the plate-shaped member 245, and providing the through holes 276 and 277 having larger diameters than the diameter of the through hole 275 in the first and second semispherical members 246 and 247.

Figure 32:
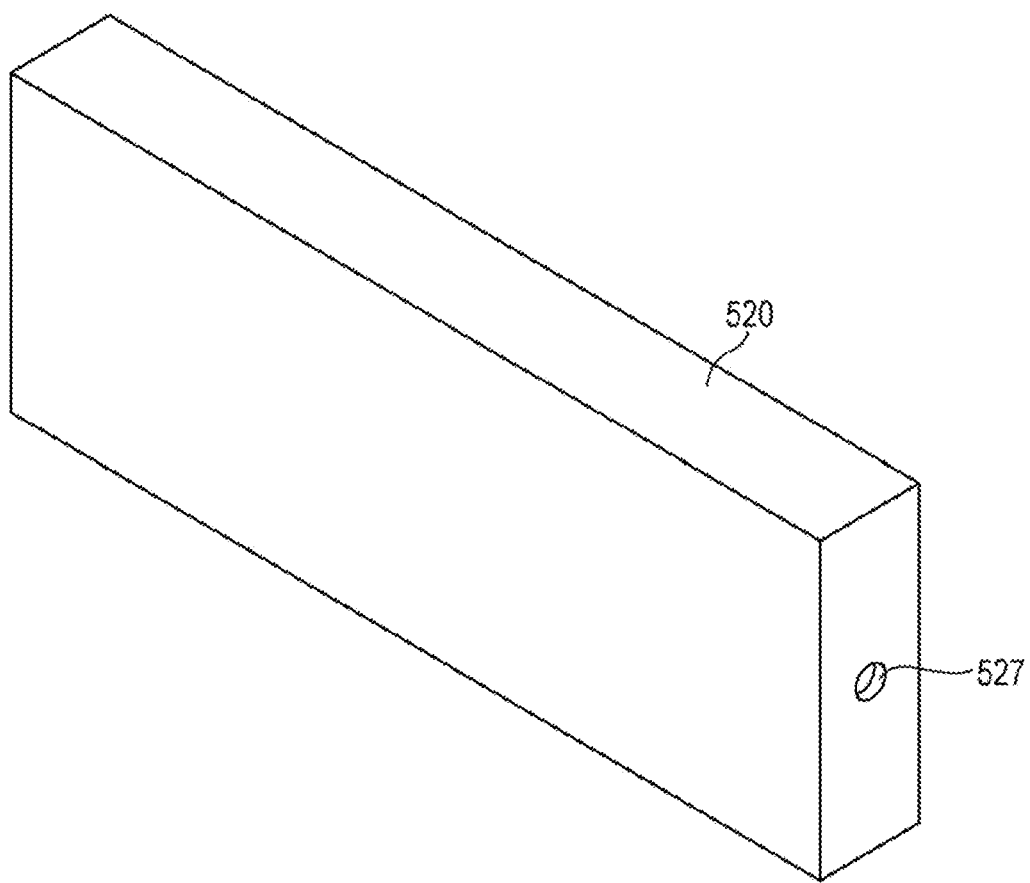
FIG. 32 is a view of a step illustrating the method of producing the flow cell according to the seventh embodiment of the present disclosure.

The plate-shaped member 245 having the through hole 275 may be produced by a drawing method. For example, a glass base material 520 having a through hole 527 having a circular section as illustrated in FIG. 32 is prepared. The glass base material 520 is heated and drawn in the same direction as the extending direction of the through hole 527. Thus, the size of the glass base material 520 is reduced in section, and the diameter of the through hole 527 becomes equal to that of the through hole 275 of the plate-shaped member 245 to be produced illustrated in FIG. 26. After that, the plate-shaped member 245 illustrated in FIG. 26 is cut from an end portion of the glass base material 520 illustrated in FIG. 32. The plate-shaped member 245 having been cut may be ground.

Figure 23:
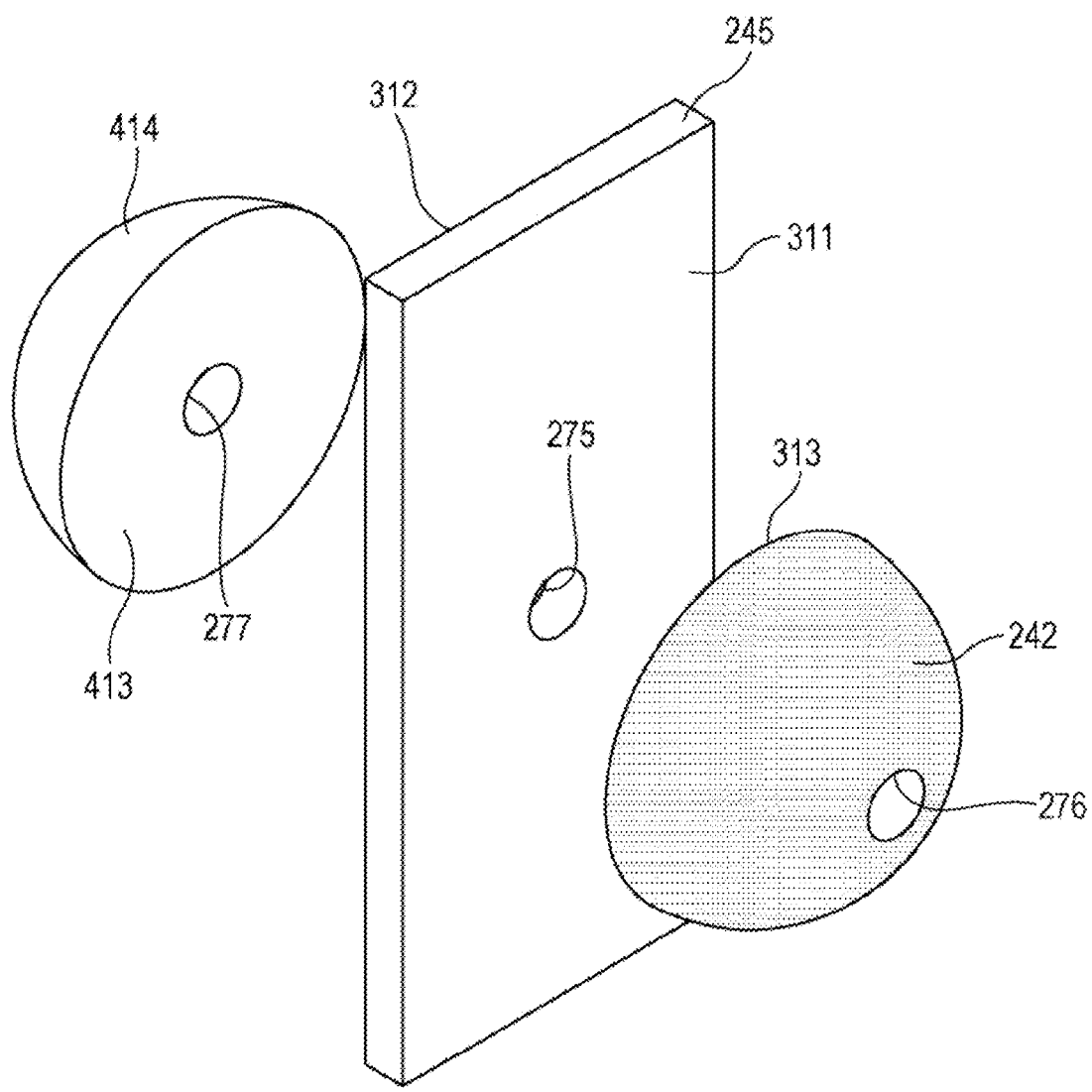
FIG. 23 is an exploded view of the flow cell according to the seventh embodiment of the present disclosure.
Figure 24:
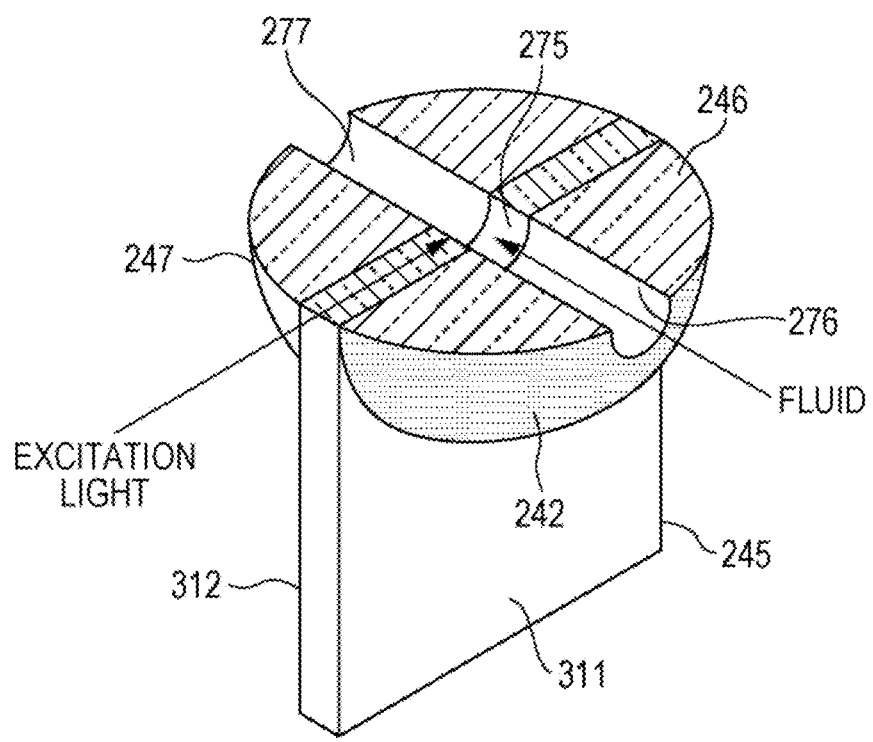
FIG. 24 is a schematic sectional view of the flow cell according to the seventh embodiment of the present disclosure seen in a XXIV-XXIV direction indicated in FIG. 22.

The plate-shaped member 245 and the first and second semispherical members 246 and 247 illustrated in FIG. 23 are positioned so as to allow the through holes 275, 276, and 277 to communicate with one another and are joined to one another by, for example, optical contact. Alternatively, the plate-shaped member 245 and the first and second semispherical members 246 and 247 may be bonded to one another with an optical adhesive or the like. Thus, the flow cell 240 according to the seventh embodiment is obtained.

With the above-described method of producing the flow cell 240 according to the seventh embodiment, by attaching the plate-shaped member 245 and the first and second semispherical members 246 and 247 to one another, the spatially shaped flow cell including the lens portion that is difficult to be integrally formed by molding can be produced.

Furthermore, when it is attempted that a through hole having corners between inner walls is provided in a member, cracking and formation of gaps tend to occur at the corners. In contrast, with the method of producing the flow cell 240 according to the seventh embodiment, the through holes 275, 276, and 277 having circular sectional shapes are formed. Thus, the occurrences of cracking and the formation of the gaps in the inner walls of the through holes 275, 276, and 277 can be suppressed.

Furthermore, difficulty in providing a through hole having a highly smooth inner wall in a member increases as the diameter of the through hole reduces and as the thickness of the member increases. Thus, it is difficult to improve the smoothness of the inner wall by, for example, grinding the inner wall of a through hole of a small diameter provided in the base material of the flow cell after the base material of the flow cell has been integrally formed. In contrast, with the above-described method of producing the flow cell 240 according to the seventh embodiment, by attaching to one another the plate-shaped member 245 and the first and second semispherical members 246 and 247 in which the through holes 275, 276, and 277 have been provided in advance, the diameter of the through hole 275 irradiated with the excitation light can be reduced and the smoothness of the inner wall of the through hole 275 irradiated with the excitation light can be improved.

Eighth Embodiment

Figure 33:
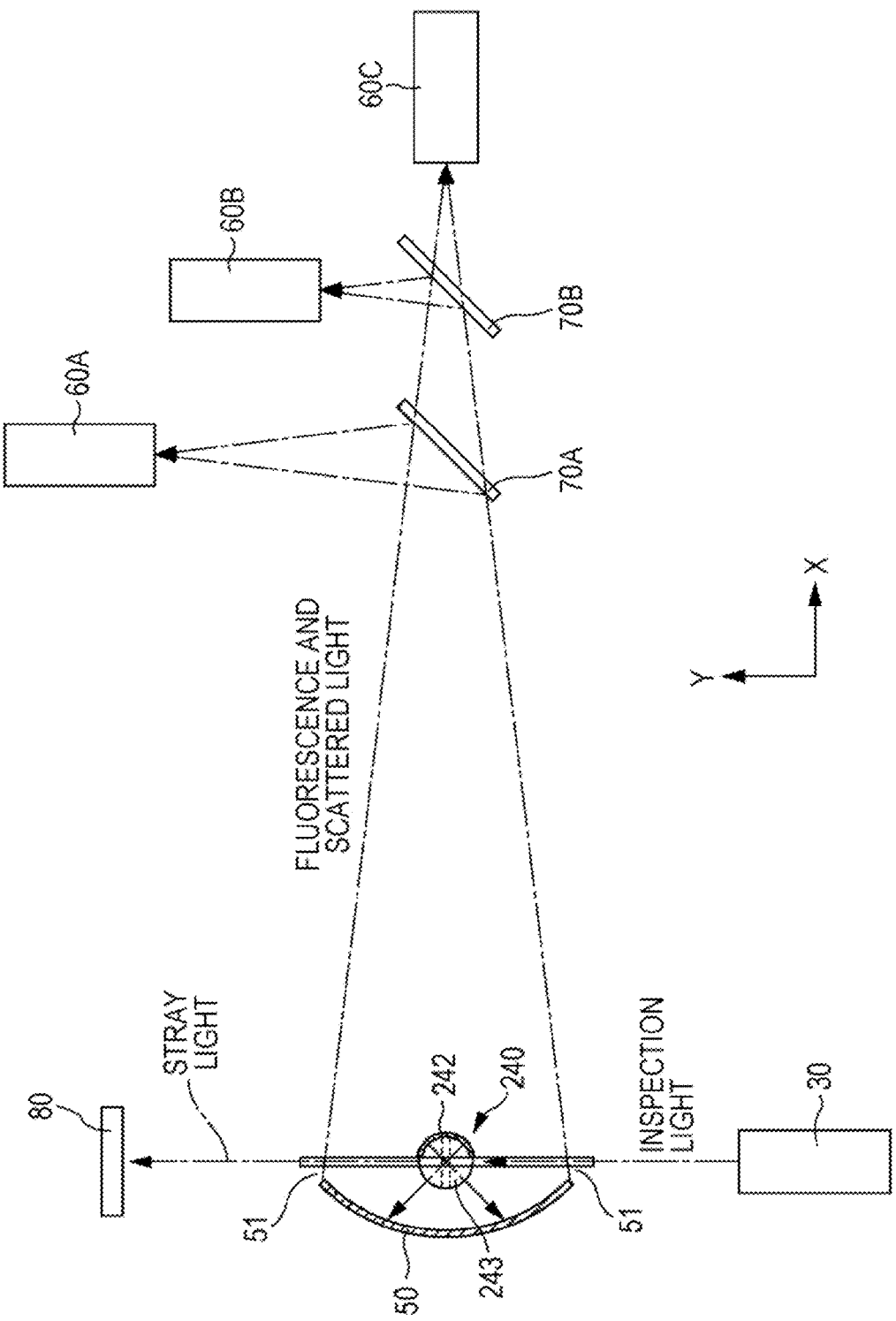
FIG. 33 is a schematic view of a particle detector according to an eighth embodiment of the present disclosure.
Figure 34:
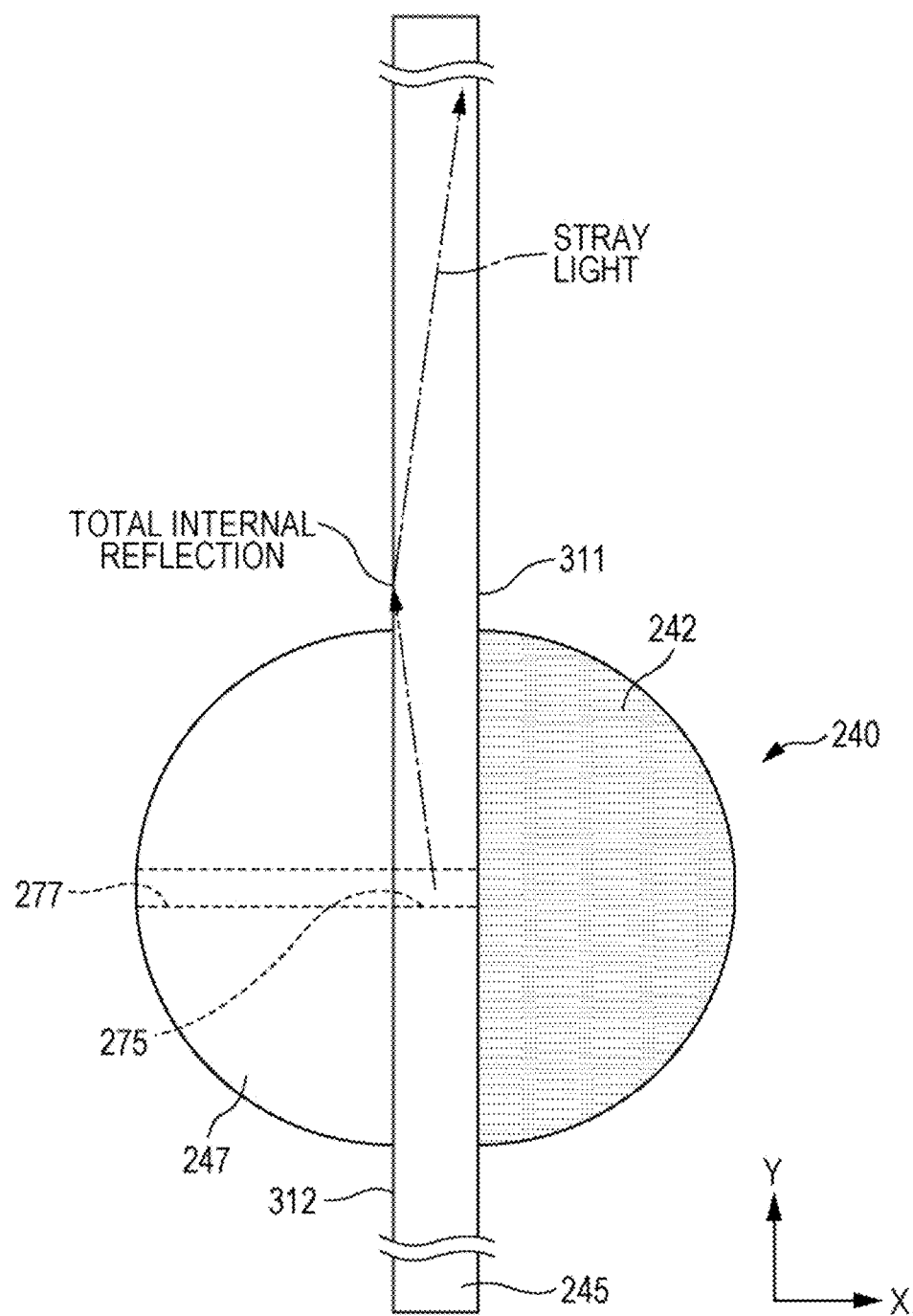
FIG. 34 is a schematic top view of the flow cell according to the eighth embodiment of the present disclosure.

In the flow cell 240 of a particle detector according to an eighth embodiment illustrated in FIG. 33, the widths of the first main surface 311 and the second main surface 312 of the plate-shaped member 245 are, as illustrated in FIG. 34, larger than the diameters of the bottom surfaces of the first semispherical member 246 on which the semispherical reflective film 242 is provided and the second semispherical member 247. Portions of the plate-shaped member 245 beyond the widths of the first and second semispherical members 246 and 247 serve as projections of the flow cell 240. As illustrated in FIG. 33, the projections of the flow cell 240 include part of a plane including the optical path of the inspection light and are perpendicular to the extending direction of the through hole 275 of the flow cell 240 illustrated in FIG. 34.

As has been described, when the flow cell 240 is irradiated with the inspection light, the stray light may be generated due to reflection and refraction of the inspection light at a curved interface between the inner wall of the through hole 275 having a circular section and the fluid in the through hole 275. The stray light tends to diverge in the sector shape having a vertex angle of about 30 to 60 degrees from a vertex at the intersection point of the inspection light and the through hole 275 of the flow cell 240 in a plane perpendicular to the extending direction of the through hole 275 of the flow cell 240.

However, as illustrated in FIG. 34, the stray light obliquely incident upon an interface between the projections and outside air from the inside of the projections undergoes total internal reflection in the projections of the flow cell 240. Thus, the stray light travels inside the projections while repeatedly undergoing the total internal reflection inside the projections of the flow cell 240. Thus, the projections of the flow cell 240 provided so as to include the optical path of the inspection light function as a waveguide of the stray light. Accordingly, by setting the projections of the flow cell 240 and the elliptical mirror 50 illustrated in FIG. 33 so as not to intersect one another, the stray light is caused to exit the projections of the flow cell 240 outside the elliptical mirror 50. This can suppress reaching of the stray light to the optical detectors 60A, 60B, and 60C.

Other elements of the particle detector according to the eighth embodiment are the same as or similar to those of the seventh embodiment.

Ninth Embodiment

A particle detector according to a ninth embodiment includes, as illustrated in FIG. 35, the inspection light source 30, the flow cell 4, the stray light attenuation member 80, and the optical detector 60. The inspection light source 30 emits the inspection light. The flow cell 4 is transparent and has the through hole 14 that has a circular sectional shape and that allows the fluid containing the particles to flow therethrough. The flow cell 4 is irradiated with the inspection light in a direction perpendicular to the extending direction of the through hole 14. The stray light attenuation member 80 is disposed so as to include the sector-shaped plane 200 that has the vertex at the intersection point of the inspection light and the through hole 14 of the flow cell 4, is parallel to the optical path of the inspection light, and is perpendicular to the extending direction of the through hole 14 of the flow cell 4. The optical detector 60 is disposed farther from the flow cell 4 than the stray light attenuation member 80 in a rearward direction and detects the reaction light generated by the particles irradiated with the inspection light in the flow cell 4.

As described above, the fluorescent particles irradiated with the inspection light in the through hole 14 that serves as the inspection region emit fluorescence. Furthermore, scattered light is generated due to, for example, Mie scattering with the fluorescent particles and non-fluorescent particles irradiated with the inspection light. The fluorescence and the scattered light as the reaction light generated by the particles irradiated with light are omnidirectionally emitted from the particles.

Furthermore, when the flow cell 4 is irradiated with the inspection light, stray light may be generated due to reflection and refraction of the inspection light at the curved interface between the inner wall of the through hole 14 having a circular section and the fluid in the through hole 14. The stray light tends to diverge in a sector shape having a vertex angle of about 30 to 60 degrees from a vertex at the intersection point of the inspection light and the through hole 14 of the flow cell 4 in the plane perpendicular to the extending direction of the through hole 14 of the flow cell 4.

Although the reaction light is omnidirectionally emitted from the particles, the stray light is likely to be distributed in a plane perpendicular to the extending direction of the through hole 14 of the flow cell 4 and unlikely to be distributed in a direction parallel to the extending direction of the through hole 14 of the flow cell 4. Thus, even when the stray light attenuation member 80 is disposed so as to include the sector-shaped plane that has the vertex at the intersection point of the inspection light and the through hole 14 of the flow cell 4, is parallel to the optical path of the inspection light, and is perpendicular to the extending direction of the through hole 14 of the flow cell 4, the omnidirectionally emitted reaction light reaches a region behind the stray light attenuation member 80. Accordingly, by setting the width of the stray light attenuation member 80 to be smaller than the width of a light receiving surface of the optical detector 60 in a direction parallel to the extending direction of the through hole 14 of the flow cell 4, the reaction light passing through regions above and below the stray light attenuation member 80 can be detected by the optical detector 60.

Other elements of the particle detector according to the ninth embodiment are the same as or similar to those of the first embodiment.

Other Embodiments

Although the present disclosure has been described with the embodiments as described above, it should be understood that the description and the drawings serving as part of the present disclosure do not limit the present disclosure. One skilled in the art should clearly understand a variety of alternative embodiments, examples, and operational techniques from this disclosure. For example, the particle detector may detect only fluorescence emitted from the particles or detect only scattered light generated by the particles. It should be understood that, as described above, the present disclosure includes a variety of embodiments and the like that are not described herein.

The invention claimed is:

1. A particle detector, comprising:
   a flow cell that is transparent and includes a through hole having a circular sectional shape, the through hole being configured to allow a fluid containing a particle to flow therethrough;
   an inspection light source configured to irradiate the flow cell with inspection light in a direction perpendicular to an extending direction of the through hole, stray light being generated due to reflection and refraction of the inspection light; and
   an optical detector configured to detect reaction light generated by the particle irradiated with the inspection light in the flow cell, wherein
   the flow cell includes a semispherical reflective film that is configured to reflect the reaction light generated by the particle irradiated with the inspection light,
   the semispherical reflective film has a cut at a portion thereof where the semispherical reflective film intersects a sector-shaped plane such that the semispherical reflective film does not reflect a portion of the stray light exiting the flow cell in the sector-shaped plane and that the optical detector does not detect the portion of the stray light exiting the flow cell in the sector-shaped plane, and
   the sector-shaped plane has a vertex at an intersection point of the inspection light and the through hole of the flow cell, is parallel to an optical path of the inspection light, and is perpendicular to the extending direction of the through hole of the flow cell.

2. A particle detector, comprising:
   a flow cell that is transparent and includes a through hole having a circular sectional shape, the through hole being configured to allow a fluid containing a particle to flow therethrough;
   an inspection light source configured to irradiate the flow cell with inspection light in a direction perpendicular to an extending direction of the through hole; and
   an optical detector configured to detect reaction light generated by the particle irradiated with the inspection light in the flow cell, the reaction light exiting the flow cell so as to be angled relative to a sector-shaped plane,
   wherein the plane has a vertex at an intersection point of the inspection light and the through hole of the flow cell, is parallel to an optical path of the inspection light, and is perpendicular to the extending direction of the through hole of the flow cell, and
   wherein the flow cell includes a plate-shaped member that is transparent, is perpendicular to the through hole of the flow cell, includes a first part of the through hole, and is disposed so as to include part of a plane that includes the optical path of the inspection light.

3. The particle detector according to claim 2,
   wherein the plate-shaped member of the flow cell includes
      a first main surface, and
      a second main surface that faces the first main surface,
   wherein the first part of the through hole penetrates through the plate-shaped member from the first main surface to the second main surface, and
   wherein the flow cell further includes
      a first semispherical member that is transparent, has a second part of the through hole, and is disposed on the first main surface of the plate-shaped member such that the first part of the through hole and the second part of the through hole communicate with each other, and
      a second semispherical member that is transparent, has a third part of the through hole, and is disposed on the second main surface of the plate-shaped member such that the first part of the through hole and the third part of the through hole communicate with each other.

4. The particle detector according to claim 3, wherein a width of each of the first main surface and the second main surface of the plate-shaped member is larger than a width of a bottom surface of the first semispherical member and a width of a bottom surface of the second semispherical member.

5. The particle detector according to claim 3, further comprising:
   a semispherical reflective film that covers the first semispherical member.

6. A particle detector, comprising:
   a flow cell that is transparent and includes a through hole having a circular sectional shape, the through hole being configured to allow a fluid containing a particle to flow therethrough;
   an inspection light source configured to irradiate the flow cell with inspection light in a direction perpendicular to an extending direction of the through hole, stray light being generated due to reflection and refraction of the inspection light;
   an optical detector configured to detect reaction light generated by the particle irradiated with the inspection light in the flow cell; and
   an elliptical mirror that is configured to reflect the reaction light which exits the flow cell, wherein
   the elliptical mirror has a cut at a portion thereof where the elliptical mirror intersects a sector-shaped plane such that the elliptical mirror does not reflect a portion of the stray light exiting the flow cell in the sector-shaped plane and that the optical detector does not detect the portion of the stray light exiting the flow cell in the sector-shaped plane, and the sector-shaped plane has a vertex at an intersection point of the inspection light and the through hole of the flow cell, is parallel to an optical path of the inspection light, and is perpendicular to the extending direction of the through hole of the flow cell.

* * * * *